(12) United States Patent
Spohn et al.

(10) Patent No.: US 12,083,321 B2
(45) Date of Patent: Sep. 10, 2024

(54) SYRINGE RETENTION FEATURE FOR FLUID INJECTOR SYSTEM

(71) Applicant: BAYER HEALTHCARE LLC, Whippany, NJ (US)

(72) Inventors: Michael Spohn, Fenelton, PA (US); Kevin Cowan, Allison Park, PA (US); David Berry, Kittanning, PA (US); Keith Lipford, Baltimore, MD (US); Jonathan Reed, Baltimore, MD (US); Patrick Campbell, Pittsburgh, PA (US); Christopher Capone, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 769 days.

(21) Appl. No.: 17/272,401

(22) PCT Filed: Sep. 10, 2019

(86) PCT No.: PCT/US2019/050293
§ 371 (c)(1),
(2) Date: Mar. 1, 2021

(87) PCT Pub. No.: WO2020/055785
PCT Pub. Date: Mar. 19, 2020

(65) Prior Publication Data
US 2021/0220561 A1    Jul. 22, 2021

Related U.S. Application Data

(60) Provisional application No. 62/729,642, filed on Sep. 11, 2018.

(51) Int. Cl.
A61M 5/31    (2006.01)
A61M 5/145    (2006.01)

(52) U.S. Cl.
CPC .......... *A61M 5/31* (2013.01); *A61M 5/14546* (2013.01); *A61M 5/14593* (2013.01)

(58) Field of Classification Search
CPC . A61M 5/31; A61M 5/14546; A61M 5/14593
See application file for complete search history.

(56) References Cited

U.S. PATENT DOCUMENTS

| 352,715 A | 11/1886 | Sandmark |
| 798,093 A | 8/1905 | Dean |

(Continued)

FOREIGN PATENT DOCUMENTS

| CN | 103917269 A | 7/2014 |
| EP | 1086661 A2 | 3/2001 |

(Continued)

OTHER PUBLICATIONS

"International Preliminary Report on Patentability from PCT Application No. PCT/US2019/050293", Mar. 25, 2021.

*Primary Examiner* — Dung T Ulsh
(74) *Attorney, Agent, or Firm* — Joseph L. Kent; James R. Stevenson; David Schramm

(57) ABSTRACT

An injector system for delivering a medical fluid, the injector system including an injector configured to receive at least one syringe, the injector comprising at least one piston for releasably engaging and reciprocally driving a plunger or an end wall of the at least one syringe; and a syringe retaining interface comprising one or more retaining elements configured to engage at least a portion of a distal end portion of the at least one syringe to limit movement of the at least one syringe in a distal direction relative to the injector as the medical fluid is delivered from the reservoir via distal movement of the at least one piston.

19 Claims, 21 Drawing Sheets

(56) References Cited

U.S. PATENT DOCUMENTS

| | | |
|---|---|---|
| 937,029 A | 10/1909 | Strong et al. |
| 1,930,929 A | 10/1933 | Eisenberg et al. |
| 2,062,285 A | 12/1936 | Bergman et al. |
| 2,514,575 A | 7/1950 | Hein et al. |
| 2,592,381 A | 4/1952 | Blackman |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,935,067 A | 5/1960 | Bouet |
| 2,950,717 A | 8/1960 | Bonet |
| 3,155,281 A | 11/1964 | Stracey |
| 3,161,194 A | 12/1964 | Chapman |
| 3,161,195 A | 12/1964 | Taylor et al. |
| 3,172,577 A | 3/1965 | Hartung |
| 3,190,619 A | 6/1965 | Penney et al. |
| 3,231,139 A | 1/1966 | Bouet |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauch et al. |
| 3,557,788 A | 1/1971 | Swartz |
| 3,613,963 A | 10/1971 | Berkmuller |
| 3,618,846 A | 11/1971 | Poli |
| 3,826,409 A | 7/1974 | Chilcoate |
| 3,873,003 A | 3/1975 | Seiferth et al. |
| 3,938,514 A | 2/1976 | Boucher |
| 4,035,461 A | 7/1977 | Korth |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,171,698 A | 10/1979 | Genese |
| 4,349,129 A | 9/1982 | Amneus |
| 4,392,491 A | 7/1983 | Takasugi et al. |
| 4,411,656 A | 10/1983 | Cornett, III |
| 4,526,296 A | 7/1985 | Berger et al. |
| 4,677,980 A | 7/1987 | Reilly et al. |
| 4,753,638 A | 6/1988 | Peters |
| 4,773,458 A | 9/1988 | Touzani |
| 4,850,807 A | 7/1989 | Frantz |
| 5,000,739 A | 3/1991 | Kulisz et al. |
| 5,201,438 A | 4/1993 | Norwood |
| 5,209,372 A | 5/1993 | Norwood |
| 5,236,204 A | 8/1993 | Hempel |
| 5,238,150 A | 8/1993 | Williams |
| 5,240,130 A | 8/1993 | Osbakk |
| 5,242,422 A | 9/1993 | Schneberger et al. |
| 5,269,428 A | 12/1993 | Gilbert |
| 5,333,761 A | 8/1994 | Davis et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,573,129 A | 11/1996 | Nagata et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,899,889 A | 5/1999 | Futagawa et al. |
| RE36,377 E | 11/1999 | Gilbert |
| 5,979,326 A | 11/1999 | Ohinata |
| 6,054,194 A | 4/2000 | Kane |
| 6,062,437 A | 5/2000 | Mascitelli |
| 6,077,252 A | 6/2000 | Siegel |
| 6,105,815 A | 8/2000 | Mazda |
| 6,142,976 A | 11/2000 | Kubo |
| 6,196,999 B1 | 3/2001 | Goethel et al. |
| 6,216,915 B1 | 4/2001 | Harman et al. |
| 6,224,577 B1 | 5/2001 | Dedola et al. |
| 6,250,505 B1 | 6/2001 | Petit |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,332,876 B1 | 12/2001 | Poynter et al. |
| 6,485,471 B1 | 11/2002 | Zivitz et al. |
| 6,558,358 B2 | 5/2003 | Rosoff et al. |
| 6,578,738 B1 | 6/2003 | Keller |
| 6,620,134 B1 | 9/2003 | Trombley, III et al. |
| 6,634,524 B1 | 10/2003 | Helmenstein |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,773,417 B2 | 8/2004 | Fitzgibbons et al. |
| 6,840,164 B2 | 1/2005 | Eastman |
| 6,866,039 B1 | 3/2005 | Wright et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 7,004,213 B2 | 2/2006 | Hansen |
| 7,011,650 B2 | 3/2006 | Rosoff et al. |
| 7,101,352 B2 | 9/2006 | Dochon et al. |
| 7,192,416 B1 | 3/2007 | Lazzaro et al. |
| 7,192,549 B2 | 3/2007 | Hansen |
| 7,250,039 B2 | 7/2007 | Fitzgerald |
| 7,309,463 B2 | 12/2007 | Hansen |
| 7,419,478 B1 | 9/2008 | Reilly et al. |
| 7,513,378 B2 | 4/2009 | Mori et al. |
| 7,553,294 B2 | 6/2009 | Lazzaro et al. |
| 7,563,249 B2 | 7/2009 | Schriver et al. |
| 7,604,623 B2 | 10/2009 | Brunner et al. |
| 7,666,169 B2 | 2/2010 | Cowan et al. |
| 7,802,691 B2 | 9/2010 | Musalek et al. |
| 8,388,580 B2 | 3/2013 | Schriver et al. |
| 8,872,708 B2 | 10/2014 | Hill et al. |
| 8,882,708 B2 | 11/2014 | Hieb et al. |
| 8,945,051 B2 * | 2/2015 | Schriver ............... A61M 5/142 604/131 |
| 9,173,995 B1 | 11/2015 | Tucker et al. |
| 9,180,252 B2 | 11/2015 | Gelblum et al. |
| 9,199,033 B1 | 12/2015 | Cowan et al. |
| 9,474,857 B2 | 10/2016 | Riley et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,507,319 B2 | 12/2019 | Haury et al. |
| 10,583,256 B2 | 3/2020 | Berry et al. |
| 10,857,345 B2 | 12/2020 | Uber, III et al. |
| 10,933,190 B2 | 3/2021 | Berry et al. |
| 11,207,462 B2 | 12/2021 | Cowan et al. |
| 11,547,793 B2 | 1/2023 | Cowan et al. |
| 2004/0116893 A1 | 6/2004 | Spohn et al. |
| 2004/0122370 A1 | 6/2004 | Joyce et al. |
| 2004/0249344 A1 | 12/2004 | Nemoto et al. |
| 2009/0112087 A1 | 4/2009 | Fago |
| 2010/0091361 A1 | 4/2010 | Yuuki |
| 2010/0286650 A1 | 11/2010 | Fitzgerald |
| 2011/0009826 A1 * | 1/2011 | Lewis ............... A61M 5/31515 604/154 |

(56) References Cited

U.S. PATENT DOCUMENTS

| | | |
|---|---|---|
| 2011/0282196 A1 | 11/2011 | Martz |
| 2012/0020911 A1 | 1/2012 | Seliktar et al. |
| 2012/0209111 A1 | 8/2012 | Cowan et al. |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0204130 A1 | 8/2013 | McArthur et al. |
| 2013/0211248 A1 | 8/2013 | Cowan et al. |
| 2013/0281940 A1 | 10/2013 | Gelblum et al. |
| 2014/0124087 A1 | 5/2014 | Anderson et al. |
| 2017/0035974 A1* | 2/2017 | Berry ............... A61M 5/31513 |
| 2018/0015274 A1 | 1/2018 | Haury et al. |
| 2018/0161496 A1 | 6/2018 | Berry et al. |
| 2019/0192770 A1* | 6/2019 | Spohn ............... A61M 5/14546 |

FOREIGN PATENT DOCUMENTS

| | | |
|---|---|---|
| EP | 1572266 A2 | 9/2005 |
| EP | 1572266 B1 | 4/2008 |
| EP | 2098258 A1 | 9/2009 |
| EP | 2767299 A1 | 8/2014 |
| EP | 3057648 A1 | 8/2016 |
| FR | 1288915 A | 3/1962 |
| GB | 2214819 A | 9/1989 |
| GB | 2374143 A | 10/2002 |
| JP | 2018138230 A | 9/2018 |
| WO | 9221391 A1 | 12/1992 |
| WO | 9707841 A2 | 3/1997 |
| WO | 0204049 A1 | 1/2002 |
| WO | 2009038955 A1 | 3/2009 |
| WO | 2010004206 A2 | 1/2010 |
| WO | 2010014654 A1 | 2/2010 |
| WO | 2011129175 A1 | 10/2011 |
| WO | 2012061140 A1 | 5/2012 |
| WO | 2012155035 A1 | 11/2012 |
| WO | 2014027009 A1 | 2/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016191485 A1 | 12/2016 |
| WO | 2017040154 A1 | 3/2017 |
| WO | 2017091643 A1 | 6/2017 |
| WO | 2018053074 A1 | 3/2018 |
| WO | 2018057386 A1 | 3/2018 |
| WO | 2019152978 A1 | 8/2019 |
| WO | 2020055785 A1 | 3/2020 |
| WO | 2020055818 A1 | 3/2020 |

* cited by examiner

SYRINGE RETENTION FEATURE FOR FLUID INJECTOR SYSTEM

CROSS REFERENCE TO RELATED APPLICATIONS

This application is a U.S. national phase application under 35 U.S.C. § 371 of PCT International Application No. PCT/US2019/050293, filed Sep. 10, 2019, and claims the benefit of U.S. Provisional Application No. 62/729,642 filed on Sep. 11, 2018, the disclosures of which are hereby incorporated by reference in their entirety herein.

BACKGROUND OF THE DISCLOSURE

Field of the Disclosure

The present disclosure relates generally to syringes having a cap configured for use with fluid injectors having the one or more syringe retention features, wherein the syringe retention features engage a distal end of the syringe to limit movement of the syringe in a distal direction during a fluid injection procedure and supporting the distal end of the syringe under pressure.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, fluid injectors have at least one drive member, such as a piston, that connects to the syringe, for example via connection with a plunger or an engagement feature on a proximal end wall of the syringe. The syringe may include a rigid barrel with the syringe plunger being slidably disposed within the barrel. In some examples, the syringe may include a rolling diaphragm barrel configuration having a flexible sidewall configured to roll upon itself, where the proximal end wall of the syringe body releasably engages and interacts with the at least one drive member. The drive members drive the plungers or the rolling diaphragm/proximal end wall in a proximal and/or distal direction relative to a longitudinal axis of the barrel to draw fluid into or deliver the fluid from the syringe barrel.

Syringes for use with fluid injectors may be made of various medical-grade plastic materials with a certain minimum wall thickness. Syringe thickness is an important design factor, as fluid pressures of up to 1200 psi may be used during an injection procedure. During certain injection procedures, the syringe itself may not be capable of withstanding the high pressure without excessive radial expansion of the syringe wall under such pressure, for example, if the wall thickness is not sufficiently large. This may result in undesired changes in fluid delivery volumes and flow rates or potentially even structural failure. Fluid injectors having at least one pressure jacket have been developed for enclosing the syringe and preventing radial expansion of the syringe due to buildup of fluid pressure within the syringe. Conventional pressure jacket designs include a rigid cylindrical pressure jacket that engages a rigid cap at the distal end to maintain the syringe within the pressure jacket.

There is a current need in the art for a syringe retaining interface that assists in limiting movement of a syringe within a pressure jacket during a filling procedure or an injection fluid delivery procedure. In one example, there is a need for a syringe retaining interface that assists in limiting movement of the syringe in a distal direction relative to the pressure jacket and/or injector housing during an injection procedure.

SUMMARY OF THE DISCLOSURE

In view of the above-identified needs, provided is a system and method for retaining at least one syringe in a medical injector during injection of a medical fluid. In some examples of the present disclosure, an injector system for delivering a medical fluid may include an injector configured to receive at least one syringe, the injector comprising at least one piston for releasably engaging and reciprocally driving a plunger or an end wall of the at least one syringe, and a syringe retaining interface comprising one or more retaining elements configured to engage at least a portion of a distal end portion of the at least one syringe to limit movement of the at least one syringe in a distal direction relative to the injector as the medical fluid is delivered from the reservoir via distal movement of the at least one piston.

In another example of the present disclosure, the one or more retaining elements may be configured to engage a flange on the distal end portion of the at least one syringe. Each retaining element may include a first surface configured to engage a distal surface of the flange and a second surface to engage a proximal surface of the flange. The one or more retaining elements may be configured to engage at least a portion of a cone portion of the distal end portion of the at least one syringe. The syringe retaining interface may include a bracket that houses the retaining elements, and the one or more retaining elements may include slidable arms configured to be movable in a lateral direction relative to the longitudinal axis of the at least one syringe. The slidable arms may be movable laterally relative to the distal end portion of the at least one syringe between a first position, in which the slidable arms are disengaged from the at least a portion of the distal end portion of the at least one syringe, and a second position, in which the slidable arms are engaged with the at least a portion of the distal end portion of the at least one syringe to limit movement of the at least one syringe in the distal direction relative to the injector. The slidable arms may be movable laterally relative to the distal end portion of the at least one syringe between a first position, in which the slidable arms define an aperture that has a diameter larger than an outer diameter of the at least one syringe, and a second position, in which the diameter of the aperture is smaller than an outer diameter of the at least one syringe such that the slidable arms limit movement of the at least one syringe in the distal direction relative to the injector. The one or more retaining elements may be activated manually by an operator or automatically using at least one processor programmed or configured to operate activation of the one or more retaining elements. The syringe retaining interface may include a rotating arm operatively connected to the injector, the rotating arm may be rotatable about a longitudinal axis of the injector, and wherein the rotating arm may include the one or more retaining elements to engage the at least a portion of the distal end portion of the at least one syringe. The rotating arm may be configured to rotate between a first position, in which the one or more retaining elements are disengaged from the at least a portion of the distal end portion of the at least one syringe, and a second position, in which the retaining elements are engaged with the at least a portion of the distal end portion of the at least one syringe to limit movement of the at least one syringe in the distal direction relative to the injector. Each of the one or more retaining elements may include at least one of a cap holding arm and a flange holding arm, and wherein, when the rotating arm is positioned to engage the at least a portion of the distal end portion of the at least one syringe, the cap holding arm may engage a cap of the at least one syringe and the flange holding arm engages a flange on the at least a portion of the distal end portion of the at least one syringe. The at least one syringe may be a rolling diaphragm syringe including the end wall, wherein the rolling diaphragm syringe may be received within a pressure jacket provided on the injector.

In another example of the present disclosure, an injector system for delivering a medical fluid may include an injector configured to receive the at least one syringe, the injector comprising at least one piston for releasably engaging and reciprocally driving a plunger or an end wall of the at least one syringe, and a syringe retaining interface comprising one or more retaining elements having a retaining surface contoured to engage at least a portion of a distal end cone portion of the at least one syringe to limit the movement of the at least one syringe in the distal direction relative to the injector as the medical fluid is delivered from the reservoir via distal movement of the at least one piston.

In another example of the present disclosure, the syringe retaining interface comprises at least two retaining arms that are configured to rotate towards and away from one another, and wherein each retaining arms comprise a retaining element provided on a distal end of each respective retaining arm, the retaining arms are rotatable between a first position and a second position, wherein, as the retaining arms are rotated from the first position to the second position, the retaining elements engage the at least a portion of the distal end cone portion of the at least one syringe, and wherein, as the retaining arms are rotated from the second position to the first position, the retaining elements are disengaged from the at least a portion of the distal end cone portion of the at least one syringe. The syringe retaining interface further comprises a locking mechanism to engage with and prevent the retaining arms from separating from one another once the retaining arms have rotated into the second position. The syringe retaining interface further comprises at least one locking protrusion provided on the distal end of each retaining arm, and wherein the locking mechanism defines at least one locking groove configured to receive at least one locking protrusion to prevent the retaining arms from separating from one another. The syringe retaining interface may include at least two retaining elements, wherein the at least two retaining elements are operatively connected to a cam plate held on the injector. The cam plate may be rotatable between a first position and a second position, wherein, as the cam plate is rotated from the first position to the second position, the at least two retaining elements may engage the at least a portion of the distal end cone portion of the at least one syringe, and wherein, as the cam plate is rotated from the second position to the first position, the at least two retaining elements may be disengaged from the at least a portion of the distal end cone portion of the at least one syringe. The syringe interface further may include corresponding locking sliders for each retaining element to lock the retaining elements in place after the retaining elements have engaged the distal end cone portion of the at least one syringe. The at least two retaining elements may engage the distal end cone portion of the at least one syringe beneath a flange on the distal end cone portion of the at least one syringe. Each of the retaining elements may be operatively connected to a rotating arm operatively connected to the injector. The rotating arms may be movable between a first position, in which the rotating arms are disengaged from the distal end cone portion of the at least one syringe, and a second position, in which the rotating arms are engaged with the distal end cone portion of the at least one syringe to prevent the at least one syringe from moving in the distal direction relative to the injector. The syringe interface may include at least one corresponding locking element for each retaining element to lock the retaining elements in place after the retaining elements have engaged the distal end cone portion of the at least one syringe. The one or more retaining elements may be activated manually by an operator or automatically using at least one processor programmed or configured to operate activation of the one or more retaining elements. The at least one syringe may be a rolling diaphragm syringe including the end wall. The rolling diaphragm syringe may be received within a pressure jacket on the injector.

In another example of the present disclosure, a method of retaining at least one syringe on an injector may include providing the injector comprising the at least one syringe; providing a syringe interface with one or more retaining elements on the injector: moving the one or more retaining elements into a disengaged position to permit the at least one syringe to be inserted into the injector: inserting the at least one syringe into the injector; and moving the one or more retaining elements into an engaged position to engage at least a portion of a distal end portion of the at least one syringe to limit movement of the at least one syringe in a distal direction relative to the injector as medical fluid is delivered from a reservoir of the at least one syringe via distal movement of a plunger reciprocally movably in the reservoir of the at least one syringe. The one or more retaining elements may be rotated when moving between the disengaged position and the engaged position. The one or more retaining elements may be slid in a lateral direction when moving between the disengaged position and the engage position.

Various other aspects of the present invention are recited in one or more of the following clauses:

Clause 1: An injector system for delivering a medical fluid, the injector system comprising an injector configured to receive at least one syringe, the injector comprising at least one piston for releasably engaging and reciprocally driving a plunger or an end wall of the at least one syringe: and a syringe retaining interface comprising one or more retaining elements configured to engage at least a portion of a distal end portion of the at least one syringe to limit movement of the at least one syringe in a distal direction relative to the injector as the medical fluid is delivered from the reservoir via distal movement of the at least one piston.

Clause 2: The injector system of Clause 1, wherein the one or more retaining elements are configured to engage a flange on the distal end portion of the at least one syringe.

Clause 3: The injector system of Clause 2, wherein each retaining element comprises a first surface configured to engage a distal surface of the flange and a second surface to engage a proximal surface of the flange.

Clause 4: The injector system of any of Clauses 1 to 3, wherein the one or more retaining elements are configured to engage at least a portion of a cone portion of the distal end portion of the at least one syringe.

Clause 5: The injector system of any of Clauses 1 to 4, wherein the syringe retaining interface comprises a bracket that houses the retaining elements, and wherein the one or more retaining element comprises slidable arms configured to be movable in a lateral direction relative to the longitudinal axis of the at least one syringe.

Clause 6: The injector system of Clause 5, wherein the slidable arms are movable laterally relative to the distal end portion of the at least one syringe between a first position, in which the slidable arms are disengaged from the at least a portion of the distal end portion of the at least one syringe, and a second position, in which the slidable arms are engaged with the at least a portion of the distal end portion of the at least one syringe to limit movement of the at least one syringe in the distal direction relative to the injector.

Clause 7: The injector system of Clause 5, wherein the slidable arms are movable laterally relative to the distal end portion of the at least one syringe between a first position, in which the slidable arms define an aperture that has a diameter larger than an outer diameter of the at least one syringe, and a second position, in which the diameter of the aperture is smaller than an outer diameter of the at least one syringe such that the slidable arms limit movement of the at least one syringe in the distal direction relative to the injector.

Clause 8: The injector system of any of Clauses 1 to 7, wherein the one or more retaining elements are activated manually by an operator or automatically using at least one processor programmed or configured to operate activation of the one or more retaining elements.

Clause 9: The injector system of any of Clauses 1 to 8, wherein the syringe retaining interface comprises a rotating arm operatively connected to the injector, the rotating arm being rotatable about a longitudinal axis of the injector, and wherein the rotating arm includes the one or more retaining elements to engage the at least a portion of the distal end portion of the at least one syringe.

Clause 10: The injector system of Clause 9, wherein the rotating arm is configured to rotate between a first position, in which the one or more retaining elements are disengaged from the at least a portion of the distal end portion of the at least one syringe, and a second position, in which the retaining elements are engaged with the at least a portion of the distal end portion of the at least one syringe to limit movement of the at least one syringe in the distal direction relative to the injector.

Clause 11: The injector system of Clause 9 or 10, wherein each of the one or more retaining elements comprises at least one of a cap holding arm and a flange holding arm, and wherein, when the rotating arm is positioned to engage the at least a portion of the distal end portion of the at least one syringe, the cap holding arm engages a cap of the at least one syringe and the flange holding arm engages a flange on the at least a portion of the distal end portion of the at least one syringe.

Clause 12: The injector system of any of Clauses 1 to 11, wherein the at least one syringe is a rolling diaphragm syringe comprising the end wall, wherein the rolling diaphragm syringe is received within a pressure jacket provided on the injector.

Clause 13: An injector system for delivering a medical fluid, the injector system comprising: an injector configured to receive the at least one syringe, the injector comprising at least one piston for releasably engaging and reciprocally driving a plunger or an end wall of the at least one syringe: and a syringe retaining interface comprising one or more retaining elements having a retaining surface contoured to engage at least a portion of a distal end cone portion of the at least one syringe to limit the movement of the at least one syringe in the distal direction relative to the injector as the medical fluid is delivered from the reservoir via distal movement of the at least one piston.

Clause 14: The injector system of Clause 13, wherein the syringe retaining interface comprises at least two retaining arms that are configured to rotate towards and away from one another, and wherein each retaining arms comprise a retaining element provided on a distal end of each respective retaining arm.

Clause 15: The injector system of Clause 13 or 14, wherein the retaining arms are rotatable between a first position and a second position, wherein, as the retaining arms are rotated from the first position to the second position, the retaining elements engage the at least a portion of the distal end cone portion of the at least one syringe, and wherein, as the retaining arms are rotated from the second position to the first position, the retaining elements are disengaged from the at least a portion of the distal end cone portion of the at least one syringe.

Clause 16: The injector system of any of Clauses 13-15, wherein the syringe retaining interface further comprises a locking mechanism to engage with and prevent the retaining arms from separating from one another once the retaining arms have rotated into the second position.

Clause 17: The injector system of Clause 16, wherein the syringe retaining interface further comprises at least one locking protrusion provided on the distal end of each retaining arm, and wherein the locking mechanism defines at least one locking groove configured to receive at least one locking protrusion to prevent the retaining arms from separating from one another.

Clause 18: The injector system of Clause 13, wherein the syringe retaining interface comprises at least two retaining elements, wherein the at least two retaining elements are operatively connected to a cam plate held on the injector.

Clause 19: The injector system of Clause 18, wherein the cam plate is rotatable between a first position and a second position, wherein, as the cam plate is rotated from the first position to the second position, the at least two retaining elements engage the at least a portion of the distal end cone portion of the at least one syringe, and wherein, as the cam plate is rotated from the second position to the first position, the at least two retaining elements are disengaged from the at least a portion of the distal end cone portion of the at least one syringe.

Clause 20: The injector system of Clause 18, wherein the syringe interface further comprises corresponding locking sliders for each retaining element to lock the retaining elements in place after the retaining elements have engaged the distal end cone portion of the at least one syringe.

Clause 21: The injector system of any of Clauses 17 to 20, wherein the at least two retaining elements engage the distal end cone portion of the at least one syringe beneath a flange on the distal end cone portion of the at least one syringe.

Clause 22: The injector system of any of Clauses 17 to 21, wherein each of the retaining elements are operatively connected to a rotating arm operatively connected to the injector.

Clause 23: The injector system of Clause 22, wherein the rotating arms are movable between a first position, in which the rotating arms are disengaged from the distal end cone portion of the at least one syringe, and a second position, in which the rotating arms are engaged with the distal end cone portion of the at least one syringe to prevent the at least one syringe from moving in the distal direction relative to the injector.

Clause 24: The injector system of Clause 22, wherein the syringe interface further comprises at least one corresponding locking element for each retaining element to lock the retaining elements in place after the retaining elements have engaged the distal end cone portion of the at least one syringe.

Clause 25: The injector system of any of Clauses 17 to 24, wherein the one or more retaining elements are activated manually by an operator or automatically, using at least one processor programmed or configured to operate activation of the one or more retaining elements.

Clause 26: The injector system of any of Clauses 17 to 25, wherein the at least one syringe is a rolling diaphragm syringe comprising the end wall, wherein the rolling diaphragm syringe is received within a pressure jacket provided on the injector.

Clause 27: A method of retaining at least one syringe on an injector, the method comprising: providing the injector comprising the at least one syringe: providing a syringe interface with one or more retaining elements on the injector: moving the one or more retaining elements into a disengaged position to permit the at least one syringe to be inserted into the injector: inserting the at least one syringe into the injector: and moving the one or more retaining elements into an engaged position to engage at least a portion of a distal end portion of the at least one syringe to limit movement of the at least one syringe in a distal direction relative to the injector as medical fluid is delivered from a reservoir of the at least one syringe via distal movement of a plunger reciprocally movable in the reservoir of the at least one syringe.

Clause 28: The method of Clause 27, wherein the one or more retaining elements are rotated when moving between the disengaged position and the engaged position.

Clause 29: The method of Clause 27, wherein the one or more retaining elements are slid in a lateral direction when moving between the disengaged position and the engage position.

Further details and advantages of the various examples described in detail herein will become clear upon reviewing the following detailed description of the various examples in conjunction with the accompanying drawing figures.

BRIEF DESCRIPTION OF THE DRAWINGS

In FIGS. 1-24, like characters refer to the same components and elements, as the case may be, unless otherwise stated.

DETAILED DESCRIPTION

Figure 1:
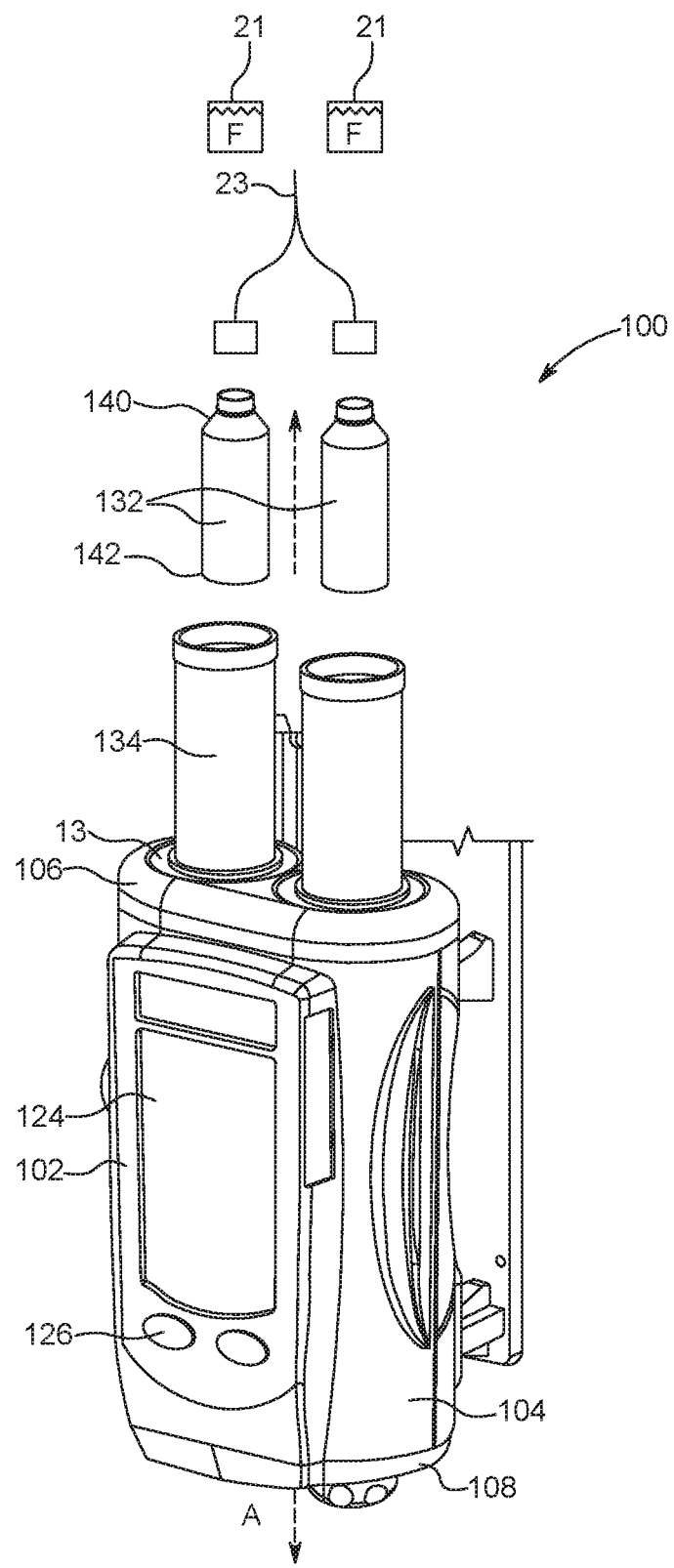
FIG. 1 is a perspective view of a fluid injector configured for use in a multi-fluid delivery system, according to one example or aspect of the present disclosure.

As used herein, the singular form of "a", "an", and "the" include plural referents unless the context clearly dictates otherwise.

Spatial or directional terms, such as "left", "right", "inner", "outer", "above", "below", and the like, relate to the invention as shown in the drawing figures and are not to be considered as limiting as the invention can assume various alternative orientations.

All numbers used in the specification and claims are to be understood as being modified in all instances by the term "about". The term "about" is meant to include plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or sub-ratios subsumed therein. For example, a stated range or ratio of "1 to 10" should be considered to include any and all subranges or sub-ratios between (and inclusive of) the minimum value of 1 and the maximum value of 10; that is, all subranges or sub-ratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to".

The term "not greater than" is synonymous with "less than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone: or B alone: or C alone: or A and B: or A and C: or B and C: or all of A, B, and C.

The term "includes" is synonymous with "comprises".

When used in relation to a syringe, for example, a rolling diaphragm syringe, the term "proximal" refers to a portion of a syringe nearest a piston element for engaging with an end wall of the syringe and delivering fluid from a syringe. When used in relation to a fluid path, the term "proximal" refers to a portion of the fluid path nearest to an injector system when the fluid path is connecting with the injector system. When used in relation to a syringe, the term "distal" refers to a portion of a syringe nearest to a delivery nozzle. When used in relation to a fluid path, the term "distal" refers to a portion of the fluid path nearest to a patient when the fluid path is connected with an injector system. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of the syringe extending between the proximal and distal ends.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

In certain embodiments, the retention features described below may engage one or more surfaces on a syringe and/or a syringe cap and maintain an outer cap assembly in an axially fixed position while allowing the syringe and an inner cap assembly to slide proximally and/or distally during an injection procedure, for example during filling and/or delivering fluid into or from the syringe. Non-limiting examples of such outer cap assemblies and inner cap assemblies are described in detail in U.S. Provisional Application No. 62/558,012 entitled "Sliding Syringe Cap For Separate Filling And Delivery", filed 13 Sep. 2017, and U.S. Provisional Application No. 62/572,062 entitled "Syringe Cap And Syringe Retaining Mechanism", filed 20 Oct. 2017, and the corresponding PCT International Application entitled "Sliding Syringe Cap For Separate Filling And Delivery", filed 12 Sep. 2018 that claims priority thereto, the disclosures of each of which are incorporated herein by this reference.

Referring to the drawings in which like reference characters refer to like parts throughout the several views thereof, the present disclosure is generally directed to a medical injector/injection system 100 (hereinafter "fluid injector system 100") for example an injector system including one or more syringes, including front-loading syringes and rolling diaphragm-type syringes. However, the various methods and protocols of the present disclosure may be utilized or incorporated into other syringe-based injector systems.

With reference to FIG. 1, the fluid injector system 100 includes multiple components as individually described herein. Generally, the fluid injector system 100 has a powered injector administrator or device configured to move various components of the injector during and injection protocol and operated by at least one processor and a fluid delivery set intended to be associated with the powered injector to take in and deliver one or more fluids from one or more fluid reservoirs under pressure into a patient. The various devices, components, and features of the fluid injector system 100 and the fluid delivery set associated therewith are likewise described in detail herein according to a non-limiting embodiment. In one example, a fluid injector system 100 may include at least one fluid reservoir, such as syringe or rolling diaphragm 132, at least one piston 16 (see FIG. 2) having an interface 14 that is reversibly connectable to a plunger of a conventional syringe or a piston engagement feature 141 of a rolling diaphragm syringe, and a fluid control module (not pictured). The at least one syringe 132 is generally adapted to interface with at least one component of the system, such as a syringe port 13 or a pressure jacket 134. The fluid injector system 100 is generally configured to deliver at least one fluid F to a patient during an injection procedure. The fluid injector system 100 is configured to releasably receive the at least one syringe 132, which is to be filled with at least one fluid F, such as a imaging contrast media, saline solution, Ringer's lactate, or any desired medical fluid, supplied by a fluid source 21 through a fluid line 23. The system may be a multi-syringe injector, wherein several syringes may be oriented side-by-side or in another spatial relationship and are separately actuated by respective pistons associated with the injector. The at least one syringe 132 may be oriented in any manner such as upright, downright, or positioned at any degree angle. In another embodiment, a fluid injector 100 may interface with one or more rolling diaphragm syringes.

Figure 2:
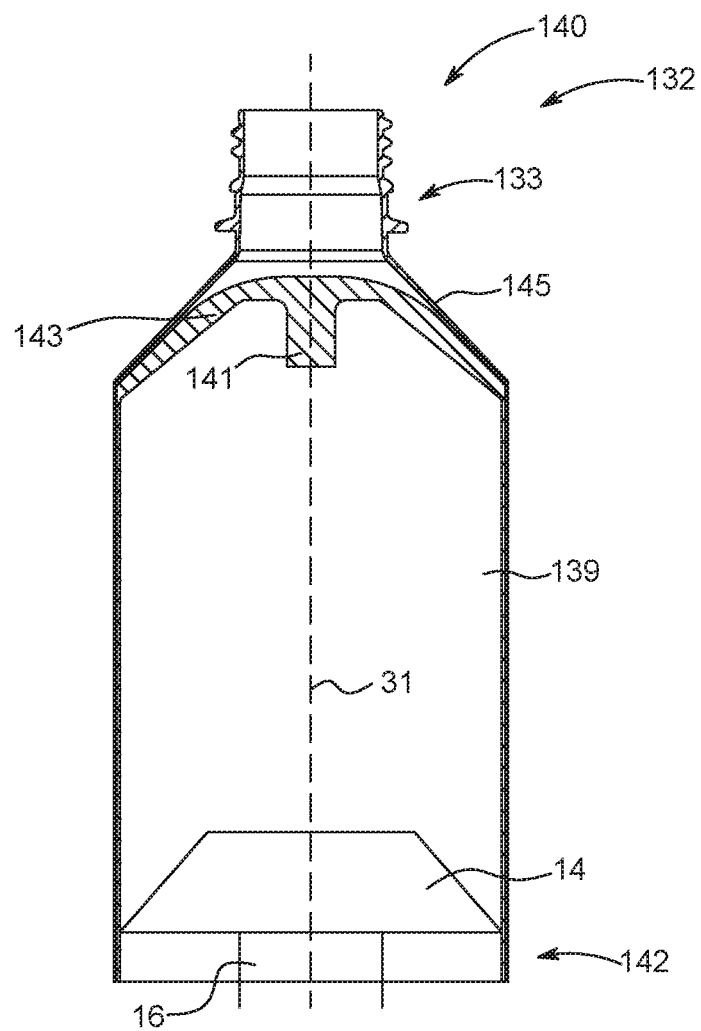
FIG. 2 is a perspective view of a syringe for use with the fluid injector of FIG. 1.

With continued reference to FIG. 1, the injector system 100 may be used during a medical procedure to inject the at least one medical fluid F into the vasculature system of a patient by driving a plunger 14 of at least one syringe 132 or a proximal end wall 143 of a rolling diaphragm syringe with a drive member, such as the at least one piston 16 (see FIG. 2). The at least one piston 16 may be reciprocally operable upon at least a portion of the at least one syringe 132, such as the plunger 14 or proximal end wall 143. Upon engagement, the at least one piston may move the plunger 14 or proximal end wall 143 toward the distal end 140 of the at least one syringe 132, as well as retracting the plunger 14 or a proximal end wall 143 toward the proximal end 142 of the at least one syringe 132. The syringe 132 extends along a longitudinal axis 31. The fluid line 23 may also be connected in fluid communication with an outlet port of each syringe 132 to place each syringe 132 in fluid communication with a catheter for delivering the fluid F from each of syringes 132 to the catheter (not shown) inserted into a patient at a vascular access site.

In various examples, the syringe retention features of the present disclosure may be suited for use in single or dual syringe-type front-loading fluid injector systems, such as are disclosed in U.S. Pat. Nos. 5,383,858, 7,553,294, 7,563,249, 7,666,169, 8,945,051, 9,173,995, 9,199,033, 9,474,857, and 10,124,110, U.S. patent application Ser. Nos. 15/305,285, 15/541,573, and 15/568,505, and in PCT Application Publication Nos. WO 2016/191485 and WO 2016/112163, the disclosures of which are incorporated herein by reference in their entireties, and in single or dual rolling diaphragm syringe-type front-loading fluid injector systems, examples of which are disclosed in International Application No. PCT/US2017/056747, WO 2016/172467, and WO 2015/164783, the disclosures of which are incorporated herein by reference in their entireties. In some examples, the syringe may be a rolling diaphragm syringe. In some examples, the syringe may be a bladder syringe described in U.S. patent application Ser. No. 13/881,072, entitled "Bladder Syringe Fluid Delivery System", or a syringe described in U.S. patent application Ser. No. 13/834,624, entitled "Bellows Syringe Fluid Delivery System", the disclosures of which are incorporated herein by reference in their entireties.

With reference to FIG. 1, the fluid injector system 100 (also referred to as "the injector") includes an injector housing 102 having opposed lateral sides 104, a distal or upper end 106, and a proximal or lower end 108. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements associated with the fluid injector system 100 described herein including communication with a controller or processor.

With reference to FIG. 1, the fluid injector system 100 includes one or more user interfaces 124, such as a graphical user interface (GUI) display window. The user interface 124 may display information pertinent to a fluid injection procedure involving the fluid injector system 100, such as current flow rate, fluid pressure, and volume remaining in the fluid sources 21 connected to the fluid injector system 100. In certain embodiments, the one or more user interfaces 124 may be at least one touch screen GUI that allows an operator to input commands and/or data for operation of the fluid injector system 100. While the user interface 124 is shown on the injector housing 102, interface 124 may also be in the form of or include an additional remote display that is wired or wirelessly linked to the housing 102 and control and mechanical elements of the fluid injector system 100. In some aspects, the user interface 124 may be a tablet computer that is detachably connected to the housing 102 and is in wired or wirelessly linked communication with the housing 102. The fluid injector system 100 may further include one or more processors in electronic communication with and configured to control one or more functions of the fluid injector system 100. Additionally, the fluid injector system 100 and/or user interface 124 may include at least one control button 126 for tactile operation by an attendant operator of the fluid injector system 100, such as a button for engaging and disengaging the syringe retention features described herein. In certain aspects, the at least one control button 126 may be part of a keyboard for inputting commands and/or data by the operator. The at least one control button 126 may be hard-wired or wirelessly connected to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) filling/purging of the fluid injector system 100: (2) inputting information and/or data related to the patient and/or injection procedure, and (3) initiating/stopping an injection procedure. The user interface 124 and/or any electronic processing units associated with the fluid injector system 100 may be wired or wirelessly connected to an operation and/or data storage system such as a hospital network system.

As used herein, the electronic control device includes a processor to, or is operable to, execute appropriate custom-designed or conventional software to perform and implement the processing steps of the embodiments of the methods and systems of the present disclosure, thereby forming a specialized and particular computing system. Accordingly, the presently-disclosed methods and systems may include one or more electronic control devices or similar computing devices having a computer-readable storage medium capable of storing computer-readable program code or instructions that cause the processing unit to execute, configure, or otherwise implement the methods, processes, and transformational data manipulations discussed hereinafter in connection with the present disclosure. Still further, the electronic control device may be in the form of a computer, a personal digital assistant, a portable computer, a laptop, a palmtop, a mobile device, a mobile telephone, a server, or any other type of computing device having the necessary processing hardware to appropriately process data to effectively implement the presently-disclosed computer-implemented method and system. In one example, the electronic control devices may be housed in the user interface 124 and corresponding processor.

Figure 3A:
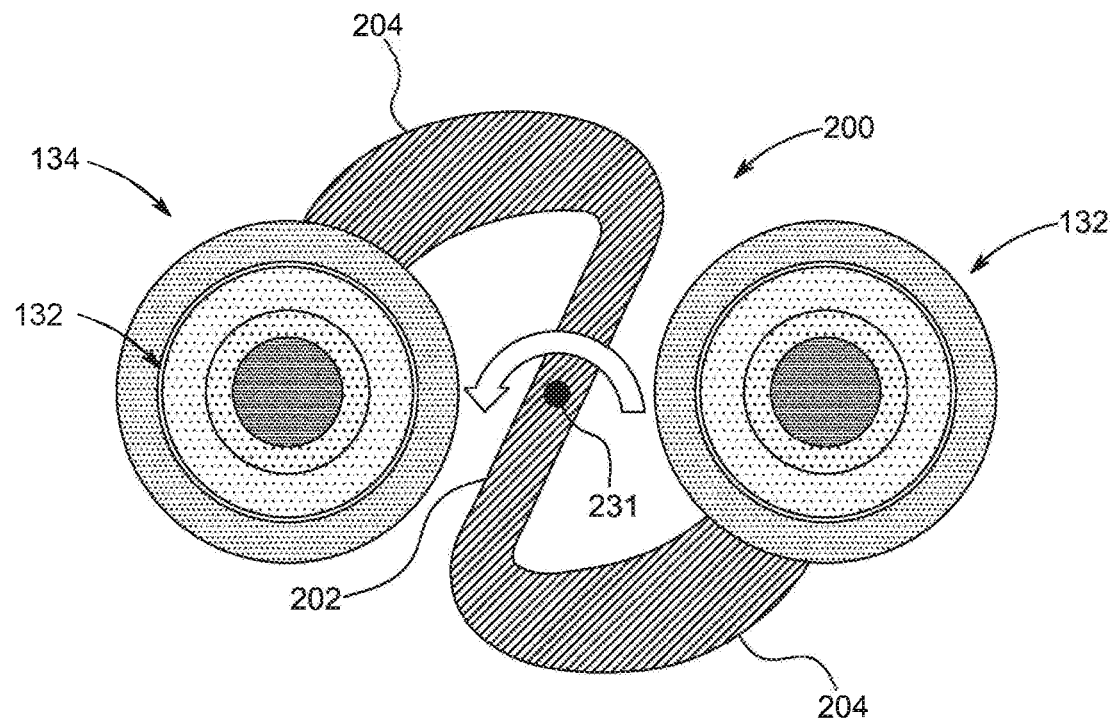
FIG. 3A is a plan view of a syringe retaining interface according to one example or aspect of the present disclosure.
Figure 3B:
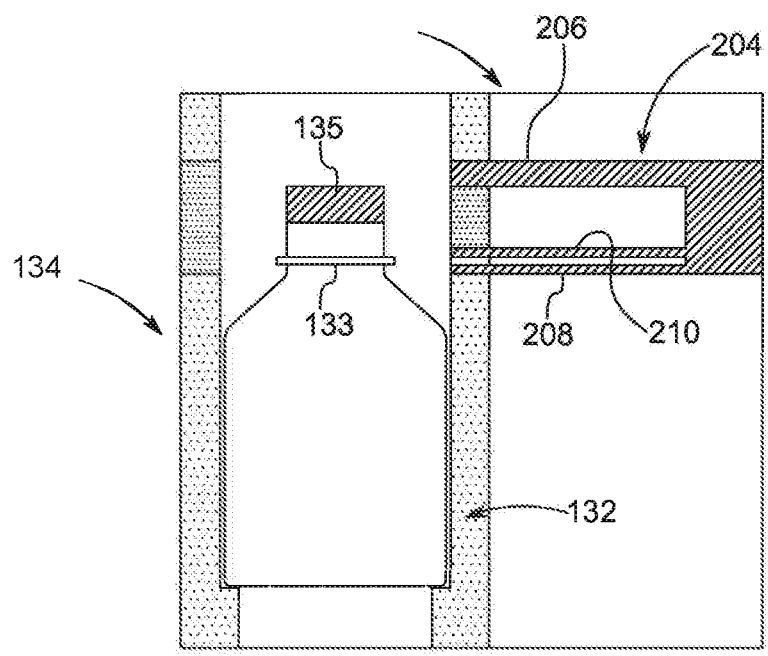
FIG. 3B is a side view of the syringe retaining interface of FIG. 3A.

With reference to FIGS. 3A and 3B, one example or aspect of a syringe retaining interface 200 is illustrated. The syringe retaining interface 200 may be provided on the fluid injector system 100 to limit movement of at least one of the syringes 132 in a distal and/or proximal direction relative to the injector housing 102 as the medical fluid is delivered from and/or drawn into the syringe interior 139 via distal and/or proximal movement of a plunger 14 within the syringe interior 139. The syringe retaining interface 200 may include at least one retaining element in the form of at least one rotating arm 202 that is operatively connected to a support surface, such as the injector housing 102, and rotatable around at least one pivot point 231. In one embodiment, the rotating arm 202 may be positioned between two syringes 132 held within pressure jackets 134 the fluid injector system 100, for example, where each syringe 132 is held within a respective pressure jacket 134. A first and second end of the rotating arm 202 may extend toward the distal ends of the first and second syringes 132, respectively. The rotating arm 202 may be rotatable about a longitudinal axis A of the injector housing 102 about pivot point 231. A distal ends of the rotating arm 202 may each include retaining elements 204 that may extend in opposite directions from one another and perpendicular to the longitudinal length of rotating arm 202.

Each of the retaining elements 204 may include at least one cap holding surface 206 and one or more syringe flange holding arms 208 spaced apart from the cap holding surface 206. The syringe flange holding arm 208 may define a slot 210 configured to receive at least a portion of a syringe flange 133 near the distal end 140 of the respective syringe 132 when in the engaged position. The rotating arm 202 is configured to rotate between at least two positions, a first position, illustrated in FIGS. 3A and 3B, in which the retaining elements 204 are each disengaged from syringe flange 133 near the distal end 140 of the respective syringes 132 and a second position, illustrated in FIGS. 4A and 4B, in which the retaining elements 204 are each engaged with syringe flange 133 near the distal end 140 of the respective syringe 132 to limit the movement of the syringe 132 in a distal and proximal directions relative to the pressure jacket 134. The rotating arm 202 may be rotated manually by a user or using the user interface 124 of the fluid injector system 100. In one embodiment, the rotating arm 202 is automatically rotated after the syringes 132 are inserted into the injector housing 102. For example, a sensor may be provided to determine that the syringes 132 have been properly inserted into the injector housing 102 and will auto-initiate the rotation of the rotating arm 202 from the first position to the second position. Once in the second position, the processor may initiate an injection protocol.

Figure 4A:
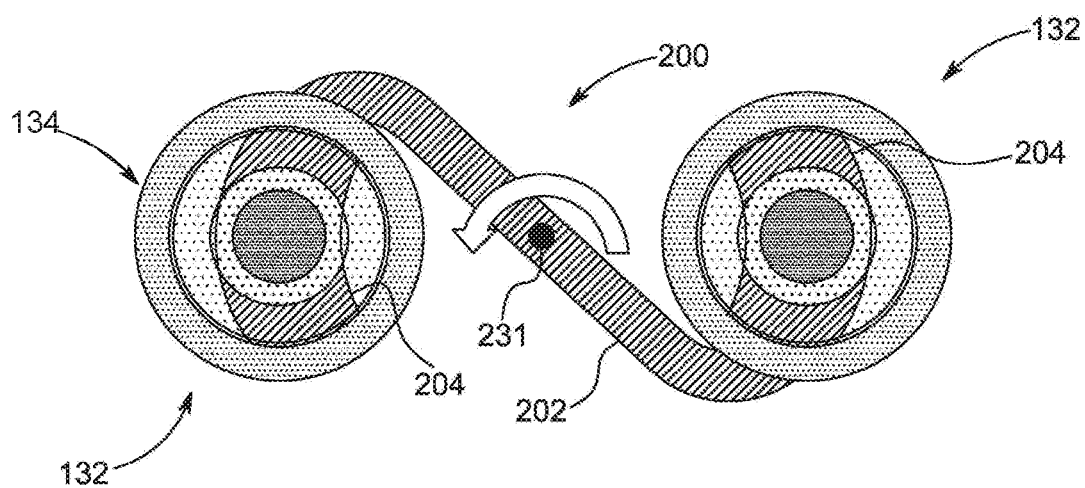
FIG. 4A is a plan view of the syringe retaining interface of FIG. 3A shown in an engaged position.
Figure 4B:
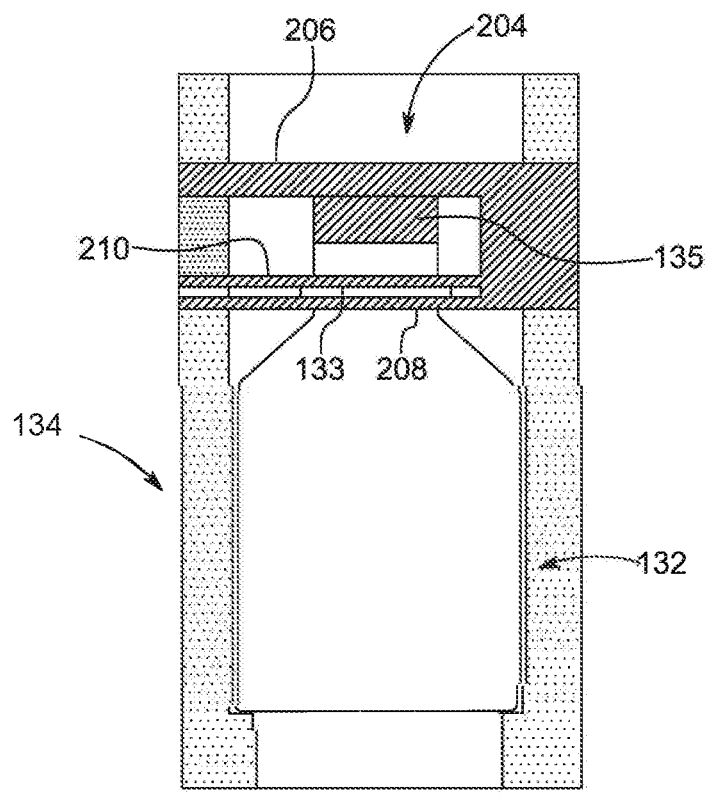
FIG. 4B is a side view of the syringe retaining interface of FIG. 3A shown in the engaged position.
Figure 5:
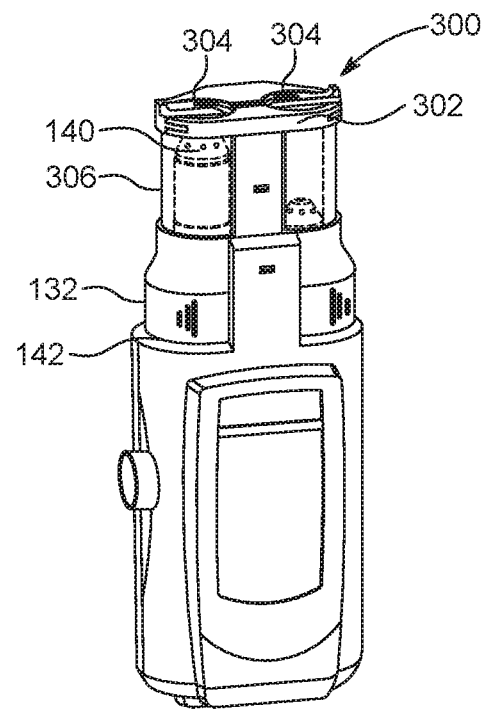
FIG. 5 is a perspective view of a syringe retaining interface according to another aspect of the present disclosure.
Figure 6:
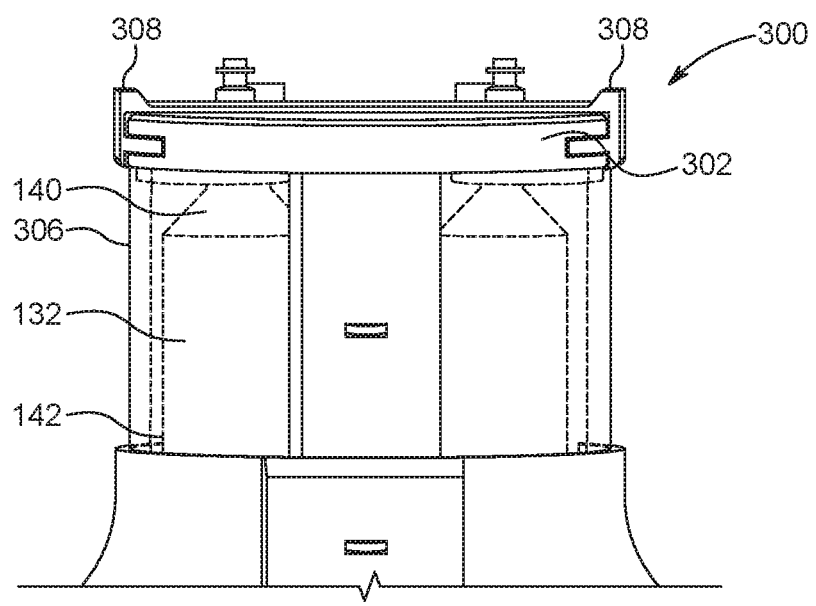
FIG. 6 is a front view of the syringe retaining interface of FIG. 5.

With reference to FIGS. 4A and 4B, the rotating arm 202 is shown in the second position in which the retaining elements 204 are engaged with syringe flanges 133 near the distal ends 140 of the syringes 132. The rotating arm 202 has been rotated about its longitudinal axis to move from the first position to the second position. As shown in FIG. 4B, once the rotating arm 202 has been rotated to the second position, the syringe flange holding arm 208 is rotated to receive and engage at least a portion of the syringe flange 133 on each of the respective syringes 132. The syringe flange 133 may be received in slot 210 defined by the syringe flange holding arm 208. A distal surface of slot 210 of the syringe flange holding arm 208 limits the movement of the syringe 132 in a distal direction, for example when the piston 16 is moved in a distal direction during a fluid delivery process, and a proximal surface of slot 210 of the syringe flange holding arm 208 limits the movement of the syringe 132 in a proximal direction, for example when the piston 16 is retracted in a proximal direction during a fluid filling process. For embodiments which utilize a rolling diaphragm syringe, proximal movement of the syringe during the filling operation must be limited to allow sufficient proximal force to be applied to the end wall of the rolling diaphragm to unroll the sidewalls of the rolling diaphragm syringe and fill the syringe 132. Furthermore, according to certain embodiments, a cap holding arm 206 may engage a distal surface of a cap 135 held on the distal end 140 of the respective syringe 132. The cap holding arm 206 may also assist in limiting the movement of the syringe 132 in a distal direction relative to the injector housing 102.

In various embodiments, distal and proximal movement of the syringe flange 133 within slot 210 of the syringe flange holding arm 208 may work in concert with an active cap 135 of the syringe to open and/or close specific fluid pathways between a fluid filling positon where the interior of the syringe is in fluid communication with a bulk fluid container and is not in fluid communication with a tubing pathway to the patient during proximal movement of the piston 16 of the injector: and a fluid delivery position where the interior of the syringe is in fluid communication with the tubing pathway to the patient and is not in fluid communication with the bulk fluid container during distal movement of the piston 16 of the injector. In certain embodiments, the active syringe cap 135 may include a third, closed position where the interior of the syringe is isolated from the bulk fluid container and the tubing pathway. Various embodiments of an active sliding syringe cap 135 moveable between a fluid filling position and a fluid delivery position with proximal and distal movement, respectively, of a piston are described in PCT International Publication No. WO 2019/055497, the disclosure of which is incorporated by reference herein.

With reference to FIGS. 5 to 8, a syringe retaining interface 300 according to another example or aspect of the present disclosure is illustrated. The syringe retaining interface 300 includes a top plate 302 of a body that may be operatively connected to or formed integral with the injector housing 102. The body extends from the proximal end of the at least one pressure jacket 306 to at least the distal end of the at least one pressure jacket 306. The top plate 302 may define a number of apertures 304 that correspond to the number of syringes 132 that can be held in the injector housing 102. For example, according to certain embodiments, the top plate 302 may define two apertures 304 which are configured to receive two syringes 132 held in pressure jackets 306 of the injector housing 102. The apertures 304 may have a diameter that is greater than an outer diameter the syringe 132 so that the syringe 132 may be readily inserted into the distal end of the pressure jacket 306 while the pressure jacket 306 is held within the injector housing 102. The at least one pressure jacket 306 may be removably inserted into the injector housing 102, for example by insertion through the apertures 304, insertion after removal of top plate 302 followed by reattachment of top plate 302, or by lateral insertion by sliding the pressure jacket 306 between the injector housing 102 and the top plate 302, for the side, front, or back of injector system 100. Pressure jacket 306 may be made of a medical grade plastic, a composite material, or metal and may be reusable over a number of injection procedures, for example being replaced monthly, bi-yearly, yearly, or after several years depending on usage of the injector system 100. The pressure jackets 306 may be of sufficient thickness and strength to limit radial expansion of the syringe 132 during an injection procedure. The pressure jacket 306 may include one or more syringe retention features that assist in retaining the syringe within the pressure jacket 306 during an injection. Non-limiting examples of suitable pressure jackets are described in PCT International Publication No. WO 2018/053074, the disclosure of which is incorporated by reference herein.

Figure 8:
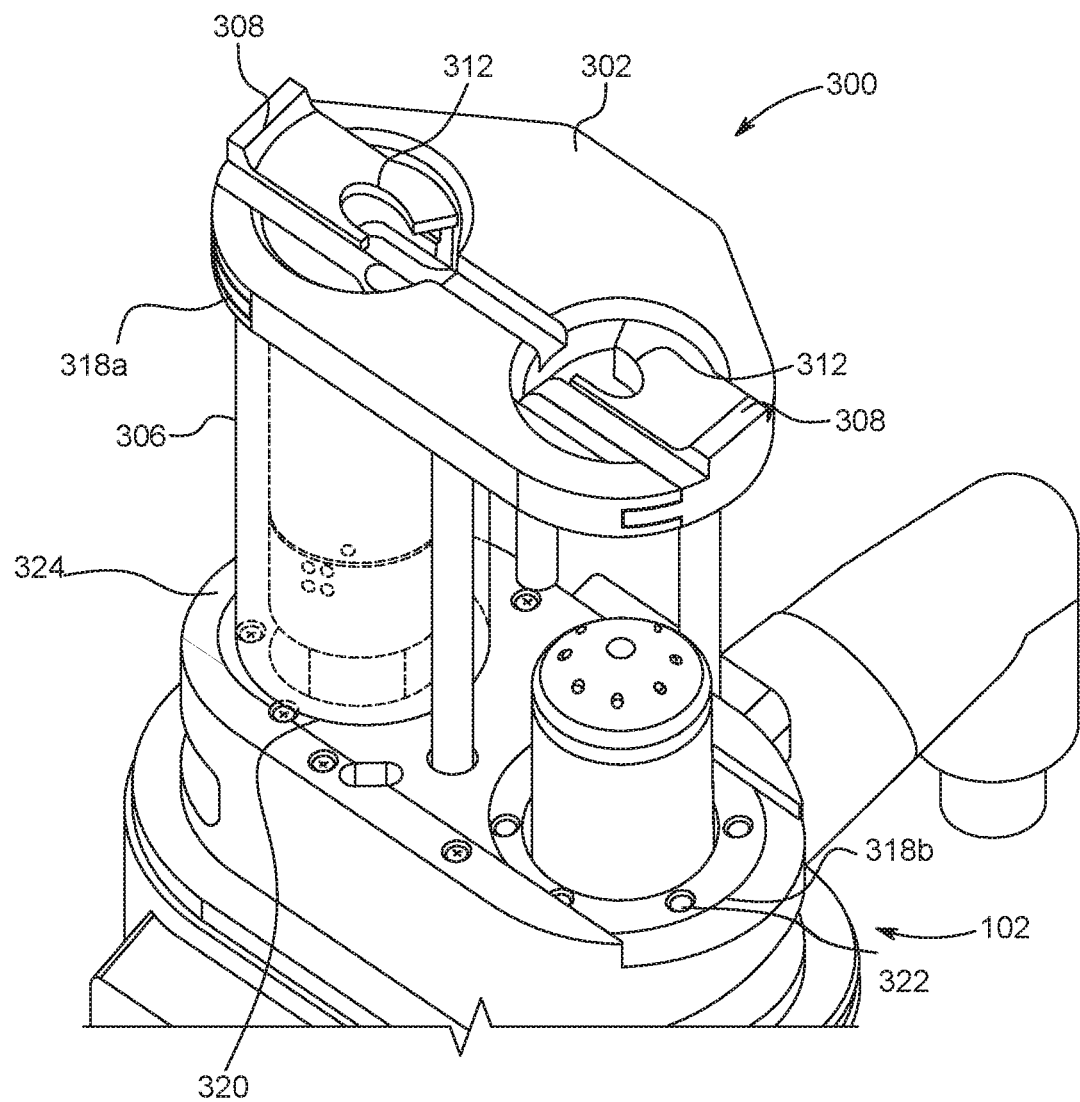
FIG. 8 is a perspective view of the syringe retaining interface of FIG. 5.

As shown in FIG. 8, the syringe retaining interface 300 may include at least one retaining element in the form of at least one slidable arm 308 that is configured to operatively engage and disengage at least a portion of a distal end portion of the at least one syringe 136, such as the syringe flange 133 and/or distal cone portion 145 (see FIG. 2) and limit movement of the syringe 132 in a distal direction relative to the injector housing 102, for example as the piston 16 is moved in a distal direction. Further, a distal at least partially circumferential surface of retaining elements may abut a proximal surface of syringe flange 133 to support the syringe 132 and limit proximal movement of the syringe during a fluid filling procedure. The slidable arms 308 may be configured to move laterally outward direction, relative to the longitudinal axis of at least one pressure jacket 306 between a first open position and a second closed position. Lateral movement of the slidable arms 308 may be in any lateral direction, for example to the sides, towards the front of the injector, and towards the back of the injector. Each slidable arm 308 is configured to move from the first open position in which the slidable arm 308 is pulled away from the pressure jacket 306 to permit insertion of the syringe 132 into the pressure jacket 306, and the second closed position in which the slidable arm 308 is moved towards and engages the distal end portion of the syringe 132 to reduce the diameter of the aperture 304 in the body 302, for example where the reduced diameter of aperture 304 is wide enough to surround a circumference of a distal tip, or cap 135 of the syringe 132, thereby limiting the movement of the syringe 132 in a distal direction relative to the injector housing 102. It is also contemplated in certain embodiments that the slidable arms 308 may assist in limiting the movement of the syringe 132 in a proximal direction relative to the injector housing 102, for example during proximal movement of the piston 16 during a filling operation. According to various embodiments, the slidable arm 308 is configured to engage at least a portion of at least one of a syringe flange 133, the cone portion 145 of the syringe 132, a syringe cap 135, or a fill valve (not shown in figures) attached to the distal end 140 of the syringe 132. In some aspects or examples, the slidable arms 308 may be moved manually by a user or by initiating one or more operations on the user interface 124 of the fluid injector system 100. In some examples or aspects, the slidable arms 308 are automatically moved to the second closed position after the syringes 132 are inserted into the injector housing 102. For example, a sensor may be provided to determine that the syringes 132 have been properly inserted into the pressure jackets 306 in the injector housing 102 and send a signal to a processor of the fluid injector system 100 to auto-initiate the movement of the slidable arms 308 from the first open position to the second closed position and further to initiate a fill/prime procedure of the syringes 132. Each of the slidable arms 308 may define at least one slot 312 configured to receive at least a portion of the syringe flange 133 or a flange on a syringe cap 135 or the active fill valve to retain the syringe 132 in the pressure jackets 306 or the proximal surface of the slidable arm 308 may have at least one conical surface configured to engage the distal end cone portion 145 of the syringe 132. A diameter of the slot 312 may be smaller than an outer diameter of the distal end cone portion 145 of the syringe 132 or an outer diameter of the fill valve 310 to prevent the distal movement of the syringe 132 or limiting the distal movement of the syringe 132. In other embodiments, the diameter may allow a the distal end cone portion 145 of the syringe to extend beyond the retention element, such that an optical air check process may be performed, as described in PCT International Publication No. WO 2017/040154 which is incorporated herein by reference. In those embodiments including at least one slot 312, distal movement of the syringe 132 may be limited by the distal surface of syringe flange 133 abutting a proximal surface of the distal slot arm and proximal movement of the syringe 132 may be limited by the proximal surface of syringe flange 133 abutting a distal surface of the proximal slot arm. In those embodiments including at least one conical surface configured to engage the distal end cone portion 145 of the syringe 132, distal movement of the syringe 132 may be limited by the distal end cone portion 145 abutting the a proximal surface of the at least one conical surface.

Figure 7:
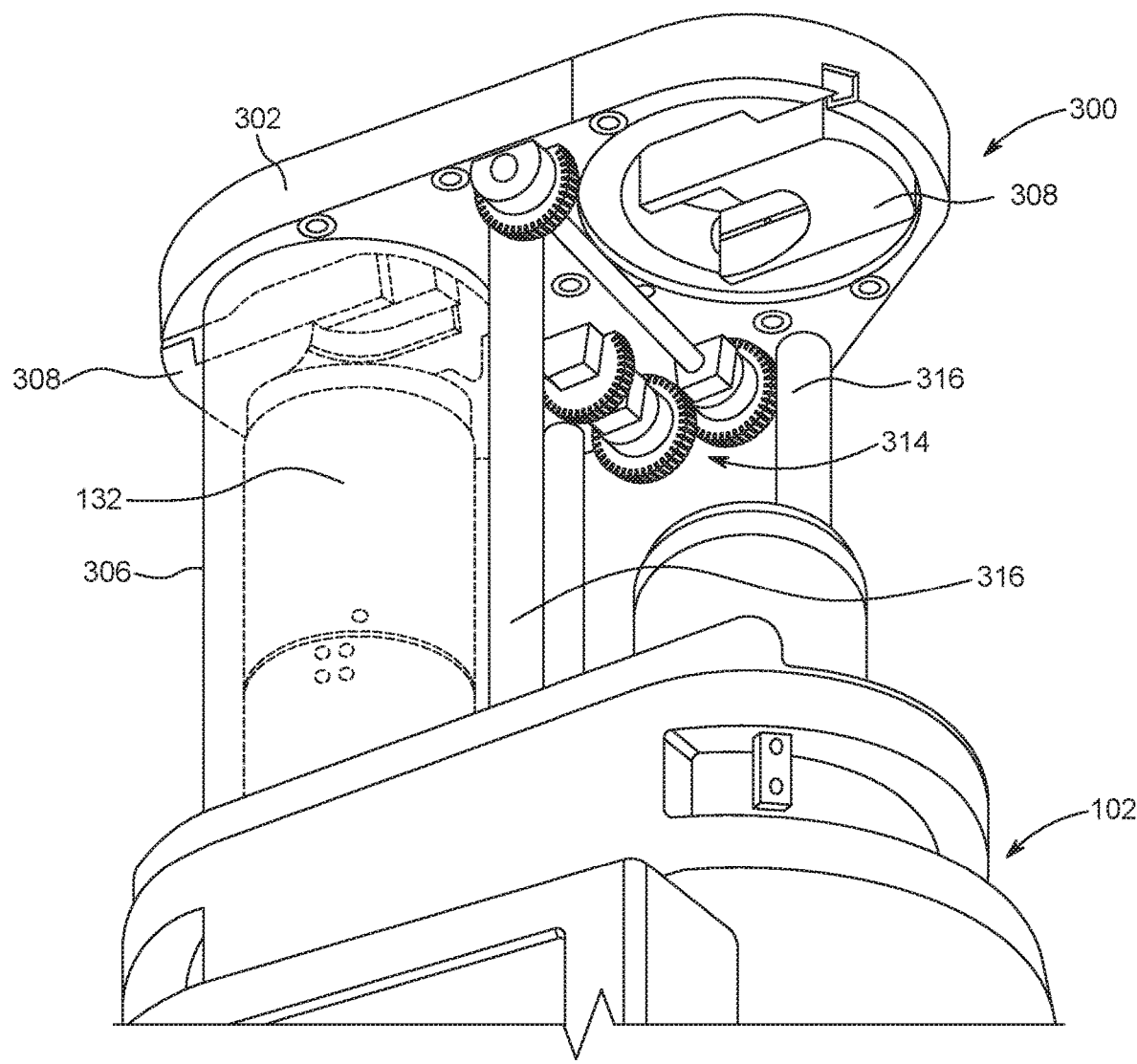
FIG. 7 is a perspective view of the internal components of the syringe retaining interface of FIG. 5.

As shown in FIG. 7, according to various embodiments, the slidable arms 308 may be operatively connected to one another using a geared arrangement 314, such that the movement of one of the slidable arms 308 between the first open position and the second closed position will cause the other slidable arm 308 to concurrently move between the first open position and the second closed position. Using the geared arrangement 314, an operator can move both slidable arms 308 or a single motor may be operated in response to pressing a button on a processor to concurrently move both arms 308. The slidable arms 308 may also be geared together for automated motor driven operation between the first open position and the second closed position. One or more sensors may be incorporated to determine position of the plates or other features of the retention mechanism. One of skill in the art will understand and a variety of gearing arrangements are possible for operation of slidable arms 308 without deviating from the intent of the present disclosure. In one certain embodiment, tension rods 316 may be positioned between a top plate 302 and a distal surface of the injector housing 102 to resist the axial forces generated during an injection or filling process of the fluid injector system 100. The tension rods 316 permit this resistance with very minimal linear and bending deflections of various features of the fluid injector system 100.

With reference to FIG. 8, according to certain embodiments, pressure jacket release plates 318a, 318b may be located on a distal surface of the injector housing 102 and a proximal surface of the top plate 302, respectively. The pressure jacket release plates 318a, 318b may encircle the receiving aperture 320 of the injector housing 102 and the aperture 304 on the top plate 302. In some examples or aspects, at least one of the pressure jacket release plates 318a, 318b may be cammed to prevent lateral movement of the pressure jacket 306 between the pressure jacket release plates 318a, 318b. In some examples or aspects, at least one of the pressure jacket release plates 318a, 318b may include a plurality of ball spring detents 322 circumferentially spaced around the pressure jacket release plate 318a, 318b to securely abut the pressure jacket 306 against the top plate 302, for example until a cam plate is rotated to lock the pressure jacket 306 in place. In some examples or aspects, at least one of the pressure jacket release plates 318a, 318b may include a retaining lip 324 that rotates relative to the pressure jacket release plates 318a, 318b to retain the pressure jacket 306 firmly in the injector housing 102.

Figure 9:
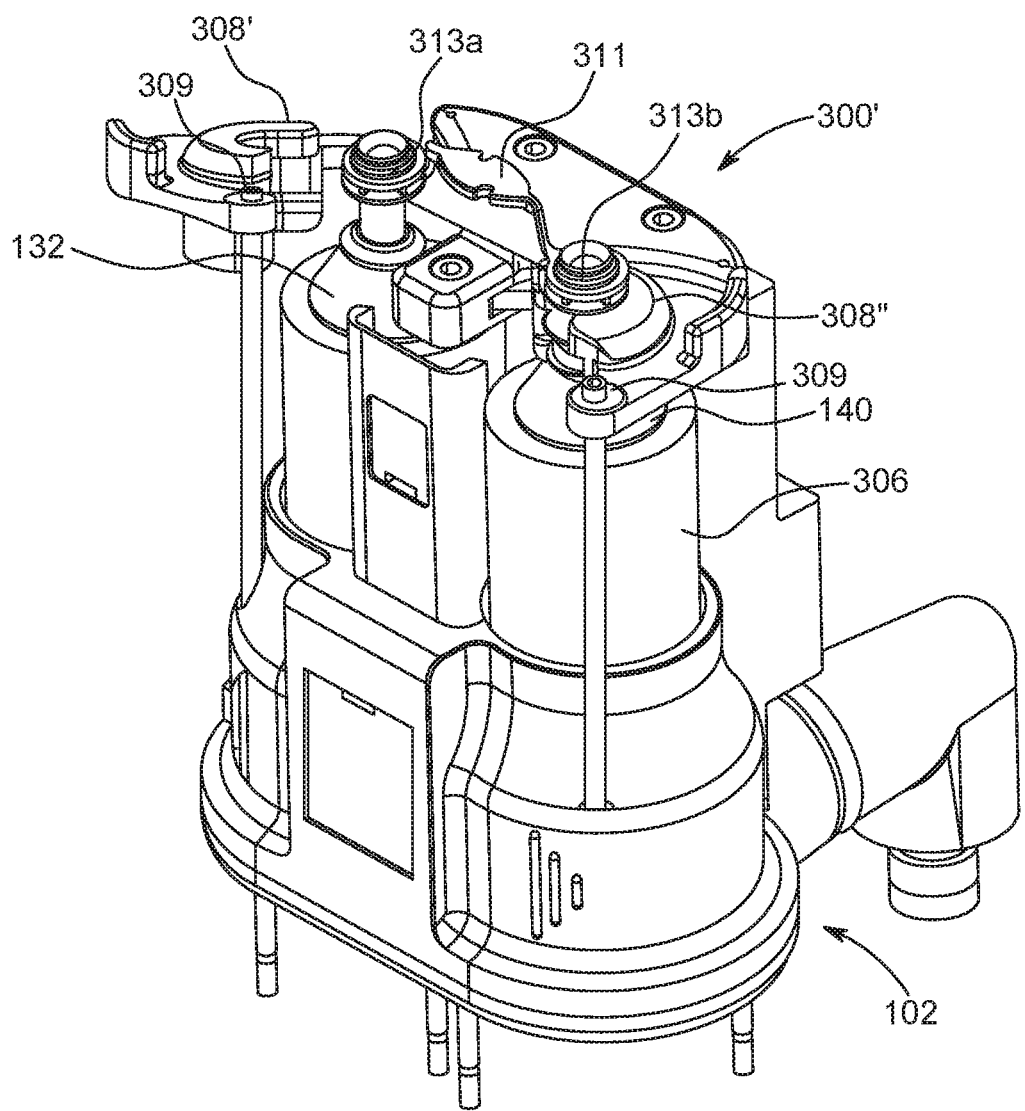
FIG. 9 is a perspective view of a syringe retaining interface according to one example or aspect of the present disclosure with a first retaining member in the open position and a second retaining member in the closed position.

With reference to FIG. 9, one aspect or embodiment of the syringe retaining interface 300' is illustrated. This aspect or embodiment of the syringe retaining interface 300' is similar in structure and operation as the syringe retaining interface 300, but includes a different arrangement for retaining the syringe 132 in the injector housing 102. In one example, instead of the slidable arms 308 included in the syringe retaining interface 300, the syringe retaining interface 300' includes at least a pair of rotating arms 308', 308". The rotating arms 308' may be configured to rotate about a pivot points 309 such that the rotating arms 308', 308" may rotated between the first open position (see rotating arm 308') and the second closed position (see rotating arm 308") where the rotating arms 308', 308" retain the syringe 132 in the pressure jacket 306 when in the second closed position and limit movement of the syringe 132 in the distal direction relative to the injector housing 102.

With continued reference to FIG. 9, in one aspect or embodiment of the syringe retaining interface 300', a retaining frame 311 may also be provided to assist in retaining the syringes 132 in the injector housing 102 and indexing the syringe relative to the pressure jacket and various injector components. The retaining frame 311 may include at least one retaining clip 313a, 313b provided on opposing ends of the retaining frame 311. The retaining clips 313a, 313b may be configured to engage with the distal end 140 of the syringe 132. In one aspect or embodiment, the retaining clips 313a, 313b may engage a cap 135 of the syringe 132, the syringe flange 133, and/or a distal end portion 140 of the syringe 132. At least a portion of the retaining frame 311 may be operatively engaged with the injector housing 102 after connection to the syringe 132. Non-limiting examples of suitable retaining frames 311 are described in co-filed PCT International Application entitled "Syringe Collar and Frame", filed Sep. 10, 2019 and claiming priority to U.S. Provisional Patent Application Nos. 62/730,153 and 62/831,004, the disclosures of these three applications are incorporated herein by this reference.

With reference to FIGS. 10 to 17, a syringe retaining interface 400 according to another example or aspect of the present disclosure is illustrated. The syringe retaining interface 400 may include a base 402 operatively connected to the injector housing 102 of the fluid injector system 100. The fluid injector system 100 may include one or more of the syringe retaining interfaces 400 depending on the number of syringes 132 to be attached. According to various embodiments, the fluid injector system 100 may include two or more syringe retaining interfaces 400 to retain two or more syringes 132. The base 402 may include a bottom member 404 and two side members 406a, 406b that extend perpendicular to the bottom member 404 for attaching one or more springs 432a, 432b, 432c to bias the syringe retaining interface to the closed position. The one or more of the components of the base 402 may be operatively connected to the injector housing 102. The base 402 may hold a pressure jacket 408 that is configured to receive and hold a syringe 132.

The syringe retaining interface 400 may also include at least two pairs of retaining arms 410a, 410b that are operatively connected to the base 402 and used to retain the syringe 132 in the pressure jacket 408. Each pair of retaining arm 410a, 410b may include at least two extension members 412a, 412b, 412c, 412d pivotably connected to the base 402. The extension members 412a, 412b, 412c, 412d may be configured to rotate towards and away from the pressure jacket 408. Each retaining arm 410a, 410b may also include a retaining element 414a, 414b operatively connected to a distal end of the respective extension members 412a, 412b, and 412c, 412d, respectively. In some examples or aspects, at least a portion of the retaining elements 414a, 414b may be made of a plastic or metal, such as stainless steel. Each retaining element 414a, 414b may form a half-circle that, when formed with the opposing retaining element 414a, 414b, creates a full circle that encompasses the distal end 140 of the syringe 132. A proximal conical surface of retaining element 414a, 414b may be configured to abut the conical shape of the distal end 140 of the syringe 132. Retaining element 414a, 414b may further include a distal surface 451a, 451b configured to abut a proximal surface of syringe flange 133 to limit proximal movement of the syringe 132.

Figure 10:
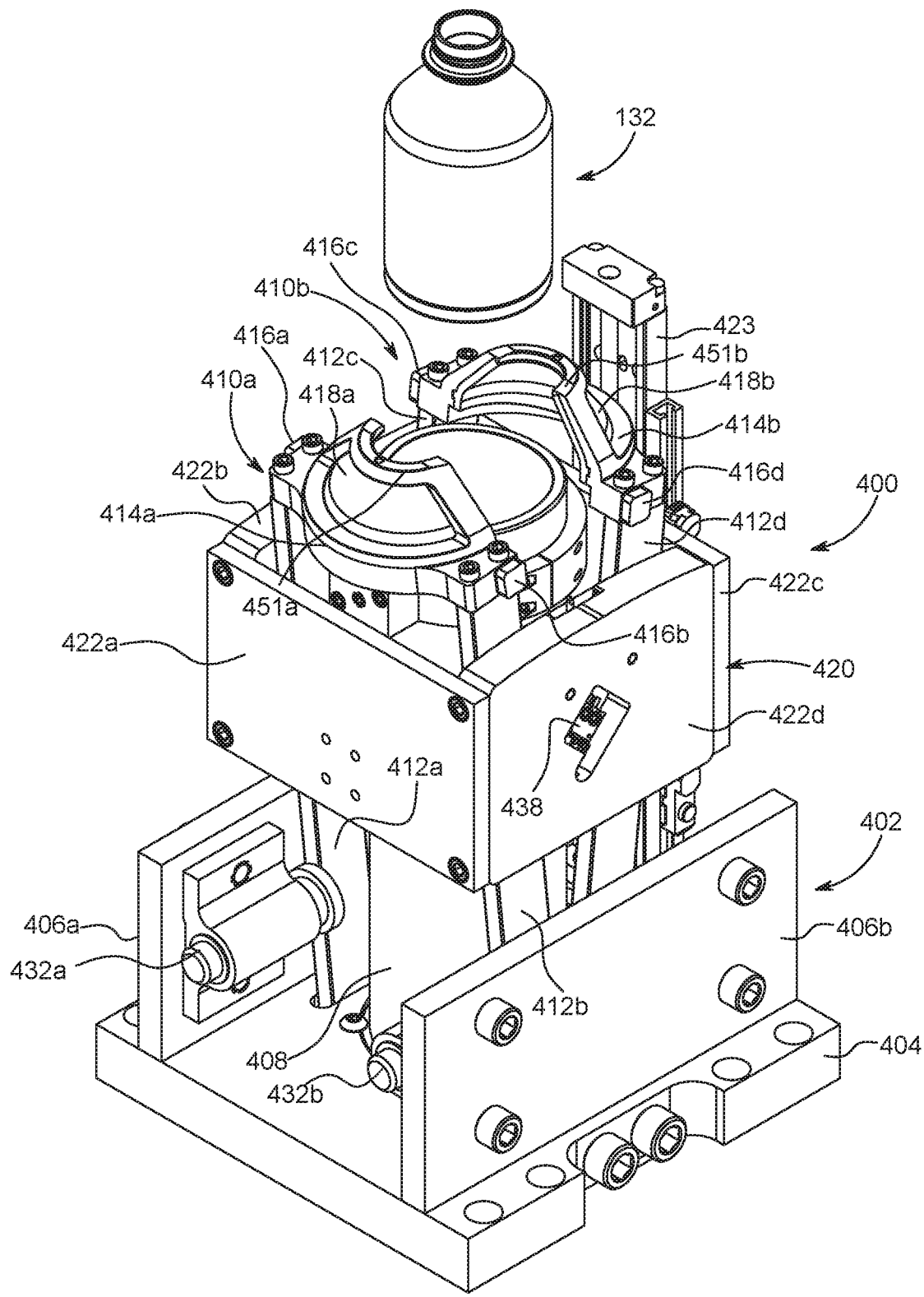
FIG. 10 is a perspective view of a syringe retaining interface according to another aspect of the present disclosure.
Figure 11:
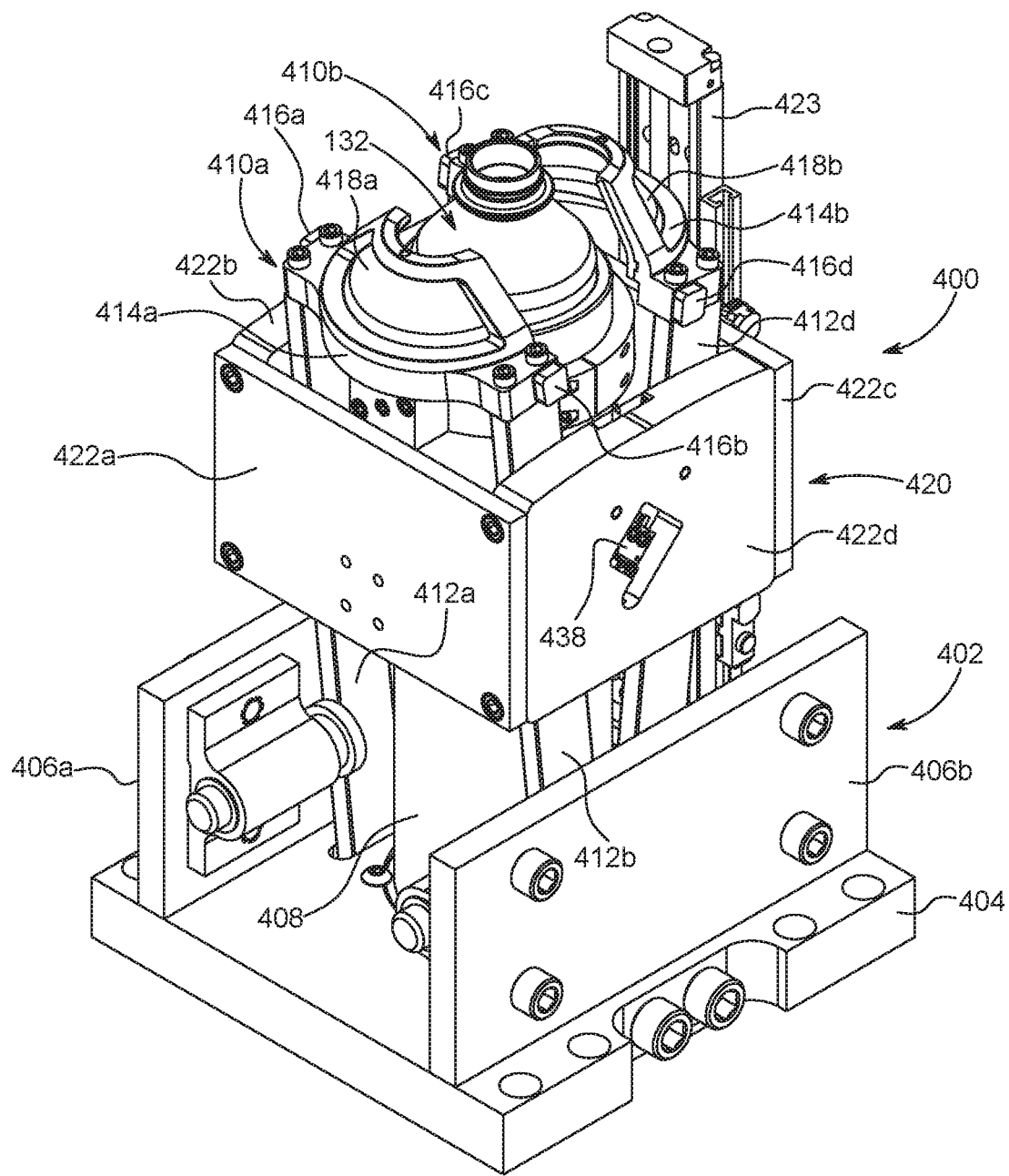
FIG. 11 is another perspective view of the syringe retaining interface of FIG. 10.

As shown in FIG. 10, each retaining arm 410a, 410b may also include a pair of locking protrusions 416a, 416b, 416c, 416d that are used to lock the retaining arms 410a, 410b in a retaining position by interaction with locking grooves 424a, 424b, as will be herein. Each retaining element 414a, 414b may also include a syringe cone support 418a, 418b positioned and held within the retaining element 414a, 414b. The syringe cone supports 418a, 418b may be made of a transparent or translucent material, such as a polymeric material to support the distal portions of the syringe 132 and allow inspection of the distal portion of the syringe 132, for example visual inspection or inspection using a camera, sensor, or other detector set up. For example, inspection of the distal portion of the syringe 132 may allow for detection of air within syringe 132 or detection of fluid type within the syringe, as described in PCT International Application Publication Nos. WO 2017/040152 and 2017/040154, the disclosures of which are incorporated by reference herein. The retaining elements 414a, 414b may surround and stiffen the syringe cone supports 418a, 418b and provide a stronger abutment surface for the conical distal end 140 of syringe 132. The retaining elements 414a, 414b and the syringe cone supports 418a, 418b may be conical in shape to correspond to the conical shape of the distal end 140 of the syringe 132. While the retaining elements 414a, 414b and the syringe cone supports 418a, 418b are illustrated as conical in shape, the shape of the syringe supports may be any shape that is contoured to match the shape of the distal end of the syringe.

As shown in FIGS. 10-17, the syringe retaining interface 400 may also include a locking mechanism 420 operatively connected to the injector housing 102 and configured to lock the retaining arms 410a, 410b in a second closed, retaining position during an injection procedure. The locking mechanism 420 may include one or more locking members 422, such as the four plate members 422a, 422b, 422c, 422d illustrated in FIG. 12 that form a substantially square cross section to receive the retaining arms 410a, 410b and pressure jacket 408 therein. While a square cross section is illustrated, other cross sections are within the scope of the present disclosure. The locking mechanism 420 may be moved distally and proximally relative to the retaining arms 410a, 410b, for example by guiding the locking mechanism 420 on a track 423 operatively connected to the injector housing 102. The locking mechanism 420 may be moved in a proximal direction and a distal direction relative to the retaining arms 410a, 410b to move between a first open, unlocked positon and a second closed, locked position, respectively. As shown in FIGS. 14-17, at least a portion of the plate members 422 may include at least one locking groove 424, for example the two of the plate members 422b, 422d may each define a locking groove 424a, 424b on an inside surface thereof to receive the locking protrusions 416a, 416b, 416c, 416d when the retaining arms 410a, 410b are held in the second closed position. Furthermore, as illustrated in FIGS. 14-17, the two plate members 422b, 422d may also each define at least two cam tracks 426a, 426b, 426c, 426d that are used to assist in moving the retaining arms 410a, 410b away and towards one another. The cam tracks 426a, 426b, 426c, 426d may receive pins 428a, 428b, 428c, 428d connected to and extend from each respective extension members 412a, 412b, 412c, 412d. According to certain embodiments, the syringe retaining interface 400 may include one or more springs 432, such as energized springs 432a, 432b, or other potential energy means that bias extension members 412a, 412b, 412c, 412d towards the second closed position while the cam tracks 426a, 426b, 426c, 426d and pins 428a, 428b, 428c, 428d may move extension members 412a, 412b, 412c, 412d towards the first open position. According to these embodiments, the springs 432a, 432b may limit the applied force necessary to close the retaining interface 400 thereby minimizing a potential pinch hazard.

Figure 12:
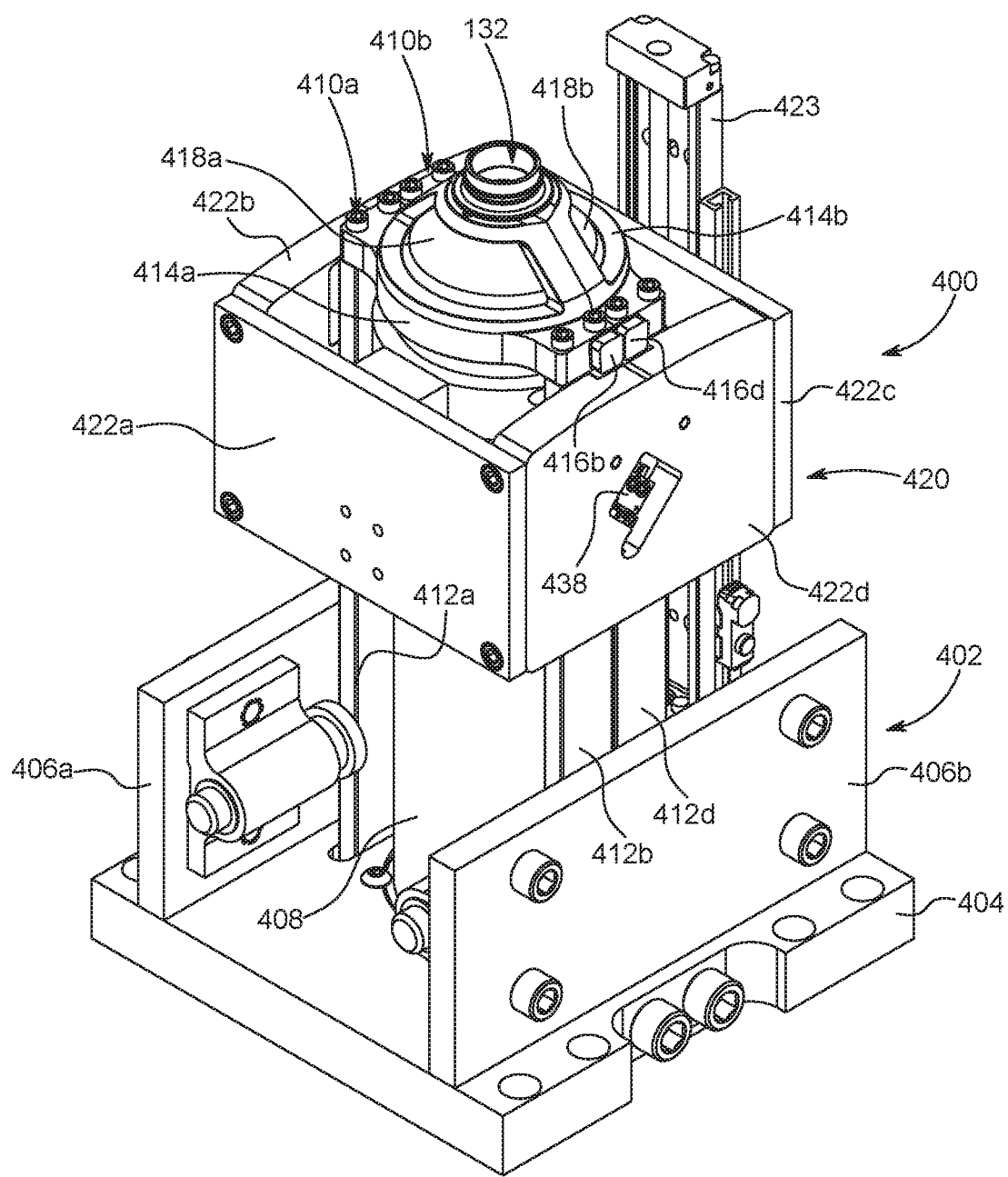
FIG. 12 is another perspective view of the syringe retaining interface of FIG. 10 in a retaining position.

With reference to FIGS. 10-17, operation of the syringe retaining interface 400 is illustrated. The retaining arms 410a, 410b are configured to move between a first open position in which the retaining arms 410a, 410b and respective retaining elements 414a, 414b are separated from one another and a second position in which the retaining arms 410a, 410b are positioned adjacent to one another to limit the movement of the syringe 132 in a distal direction relative to the injector housing 102. With reference to FIG. 10, the retaining arms 410a, 410b may be separated from one another to permit the syringe 132 to be inserted into the pressure jacket 408. In one example, the retaining arms 410a, 410b are positioned in a passively closed configuration, in which the retaining arms 410a, 410b are biased towards the second, closed position via springs 432a, 432b (see FIG. 17) that are attached to the retaining arms 410a, 410b. In one example, the springs may be compression springs. Therefore, a force must be applied to the retaining arms 410a, 410b to open the retaining elements 414a, 414b to permit insertion of the syringe 132 into the pressure jacket 408. After the syringe 132 has been inserted into the pressure jacket 408 (FIG. 11), the retaining arms 410a, 410b are moved into the second, closed position to limit the movement of the syringe 132 in the distal direction during an injector procedure of the fluid injector system 100. Further, a distal circumferential surface 451a, 451b of combined retaining elements 414a, 414b may abut a proximal surface of syringe flange 133 to support the syringe 132 and limit proximal movement of the syringe during a filling procedure, as described herein. As shown in FIG. 12, when the retaining arms 410a, 410b are moved into the second, closed and locked position (see FIG. 13), the retaining elements 414a, 414b are directed towards one another into a position in which a small gap or no gap is established between the retaining elements 414a, 414b. Due to the retaining elements 414a, 414b being positioned close to one another, the distance between the retaining elements 414a, 414b is reduced, thereby limiting the movement of the syringe 132 in a distal direction relative to the injector housing 102.

Figure 13:
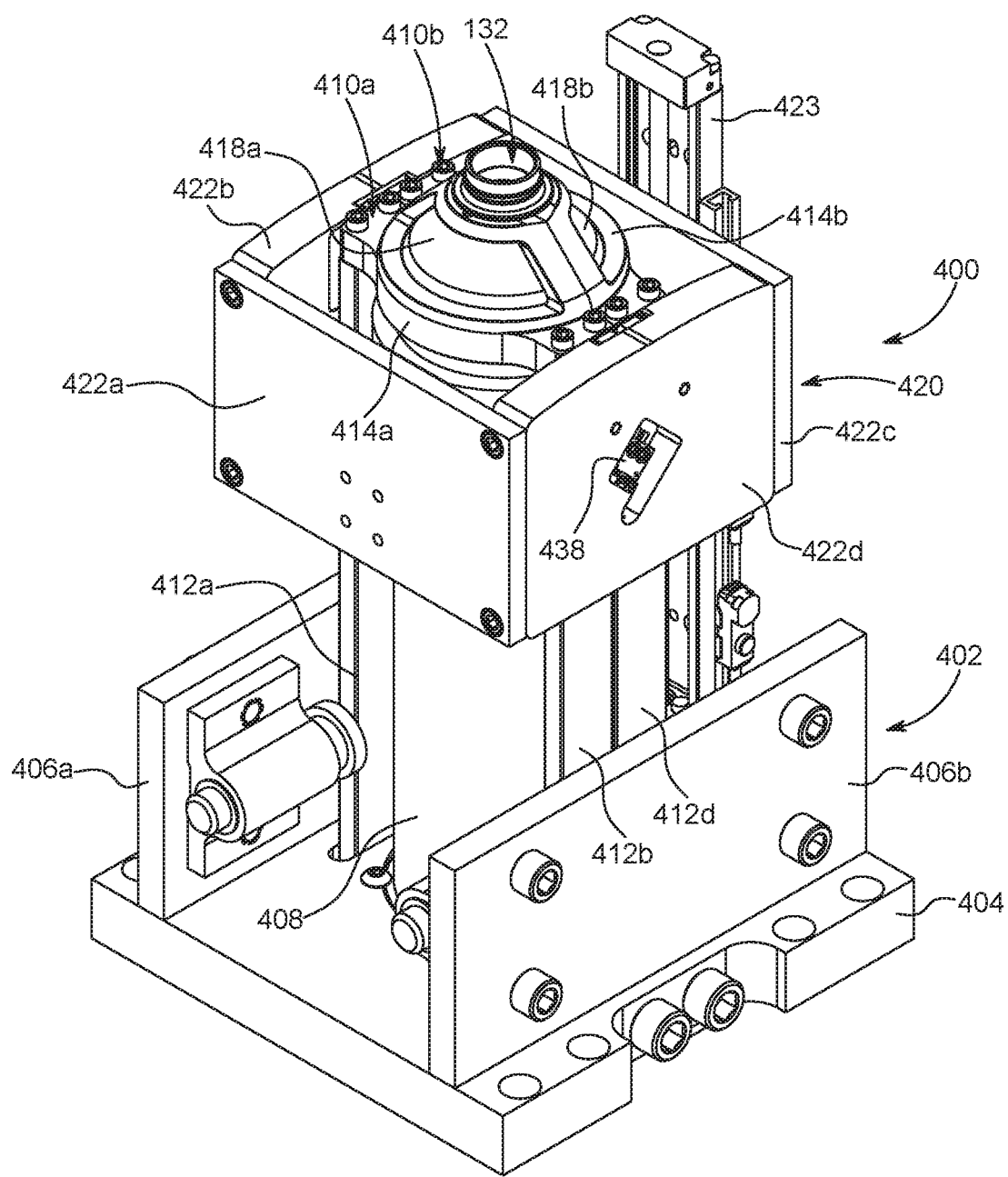
FIG. 13 is another perspective view of the syringe retaining interface of FIG. 10 in a locking position.
Figure 14:
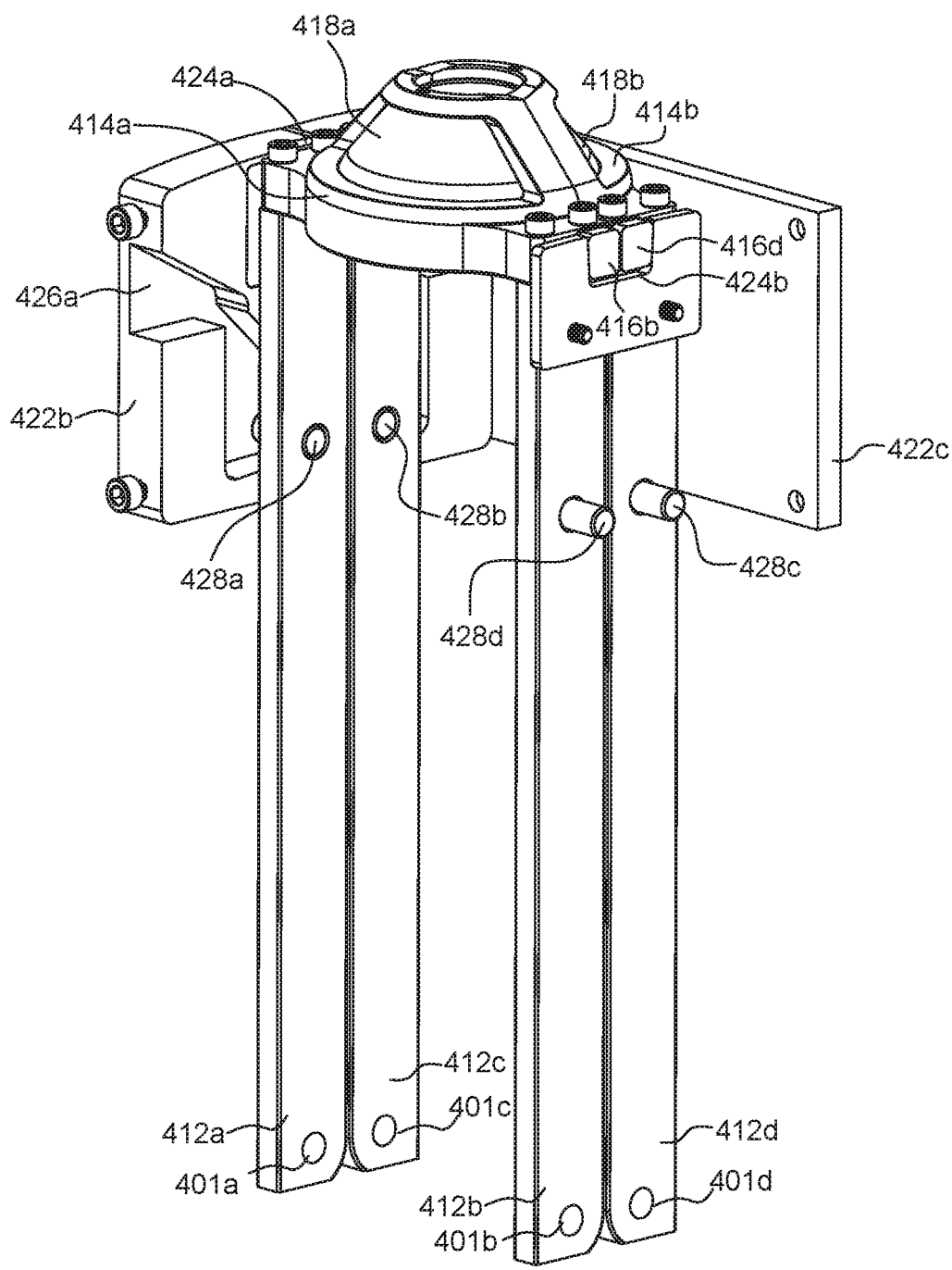
FIG. 14 is a perspective view of the retaining arms of FIG. 10 in the locking positon.

The retaining arms 410a, 410b are separated from one another to move to the first open position by applying an outward radial force to the pins 428a, 428b, 428c, 428d (FIGS. 14 to 17). For example, a motor (not shown) may apply a radial outward force to the pins 428a, 428b, 428c, 428d to move the retaining arms 410a, 410b away from one another. For example, as plates 422 are moved in the proximal direction, pins 428a, 428b, 428c, 428d interact with and ride along respective cammed surfaces 434a, 434b, 434c, 434d to move pins 428a, 428b, 428c, 428d and corresponding retaining arms 410a, 410b away from one another. In the first open position, pins 428a, 428b, 428c, 428d may ride up into upper portion 430a, 430b to lock the retaining interface 400 in the first open position. The radial outward force created by the motor overcomes the spring force provided by the springs 432a, 432b in the interface, thereby permitting the retaining arms 410a, 410b to be separated from one another. After the syringe 132 has been inserted into the pressure jacket 408 (FIG. 11), the motor may distally move 422a, 422b, 422c, 422d to retract the pins 428a, 428b, 428c, 428d from upper portion 430a, 430b and drive pins 428a, 428b, 428c, 428d along cammed surfaces 434a, 434b, 434c, 434d to the second closed position or simply permit the compression springs 432a, 432b to move the retaining arms 410a, 410b back to the second, retaining position. In some examples or aspects including the spring-driven closure of the retaining arms 410a, 410b, the closure of the retaining arms 410a, 410b is less likely to create a pinching hazard for users that may inadvertently leave their fingers positioned between the retaining elements 414a, 414b when they are closing. Further, the mechanism may also prevent the motor from moving into a locked position if there is an obstruction between the retaining elements 414a, 414b. Once the retaining arms 410a, 410b are moved into the second, retaining position, the locking protrusions 416a, 416b, 416c, 416d will be positioned adjacent one another, respectively. As shown in FIG. 13, the motor may proceed to move the locking mechanism 420 in the distal direction such that the locking protrusions 416a, 416b, 416c, 416d are received in the respective locking grooves 424a, 424b of the locking mechanism 420. When positioned with the locking grooves 424a, 424b, the locking protrusions 416a, 416b, 416c, 416d, and thereby the retaining arms 410a, 410b, are prevented from moving radially outward to the first open position, for example under the distal force applied by a piston. Instead, the retaining arms 410a, 410b are held in the second, closed position.

Figure 15:
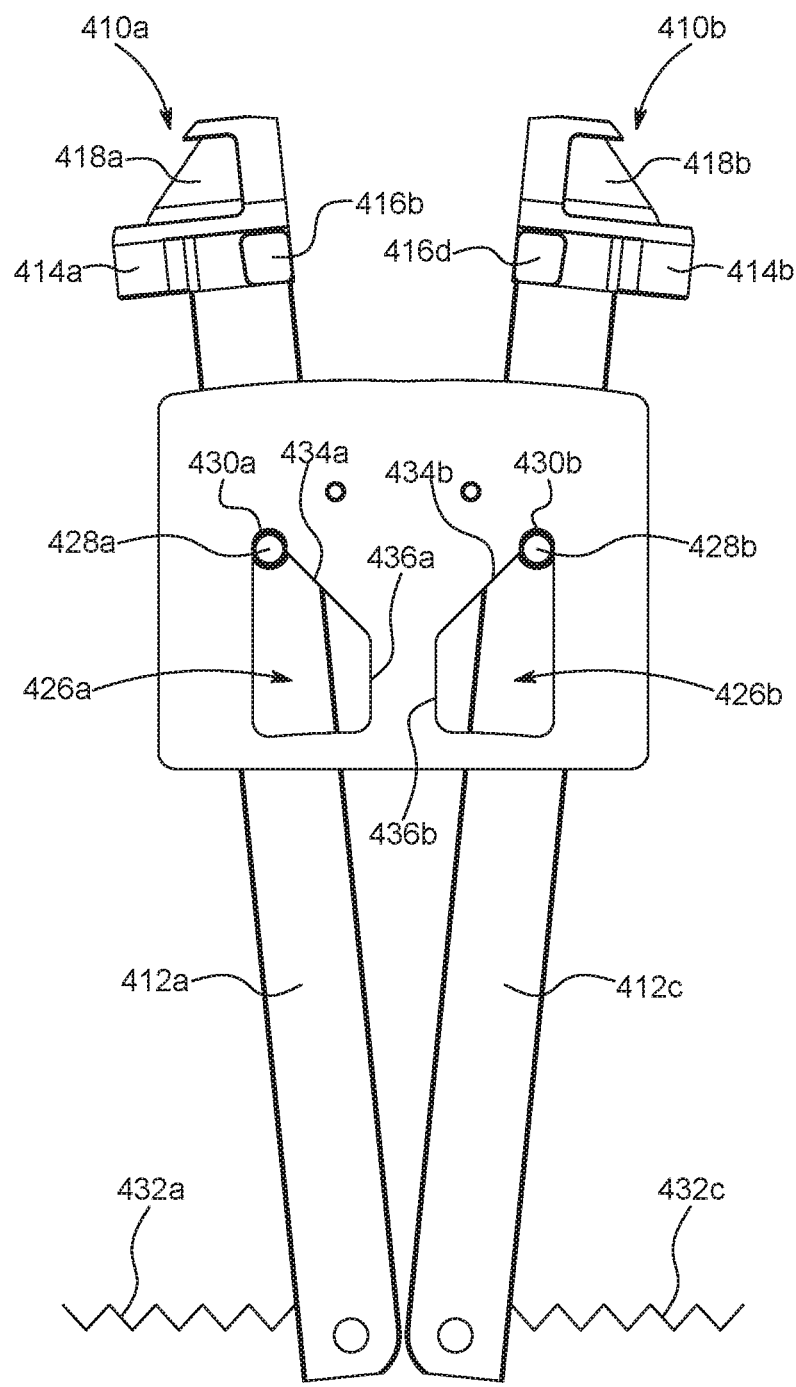
FIG. 15 is a side view of the retaining arms of FIG. 10 in the open position.

In another example of the present disclosure, instead of using a passively controlled configuration for the syringe retaining interface 400, an actively controlled configuration may be used to move the retaining arms 410a, 410b between the first open position and the second, closed position. In this actively controlled configuration, the motor fully determines and controls the position of the retaining arms 410a, 410b and the retaining elements 414a, 414b at all times. In particular, the locking mechanism 420 may be moved in a proximal and a distal direction relative to the injector housing 102 to move the retaining arms 410a, 410b away from and towards one another. As shown in FIG. 15, when the locking mechanism 420 is positioned in a lower position, the pins 428a, 428b of the extension members 412a, 412c are positioned in an upper portion 430a, 430b of the cam surfaces 434a, 434b of the locking mechanism 420. The upper portion 430a, 430b constrains the pins 428a, 428b from moving in any radial direction, thereby preventing the retaining arms 410a, 410b from inadvertently moving outwardly or inwardly relative to the pressure jacket 408. By moving the pins 428a, 428b into the upper portions 430a, 430b of the cam tracks 426a, 426b, the retaining arms 410a, 410b are held in the first open position to permit a user to insert a syringe 132 into the pressure jacket 408. Alternatively, in another embodiment of a syringe retaining interface 400' without compression springs 432a, 432b but otherwise having similar features except with respect to a second proximal cam track 426a, 426b is illustrated in FIG. 16B. The syringe retaining interface 400' includes the second proximal cam track 426a, 426b having a slope complementary to cam tracks 434a'. 434b' but abutting the proximal side of pins 428a', 428b' which may allow a motor to move the retaining arms 410a', 410b' towards one another such that the pins 428a', 428b' are directed along an intermediate sloped portions of the second proximal cam tracks 426a, 426 and the retaining arms 410a', 410b' move from the first open position to the second closed position.

Figure 16A:
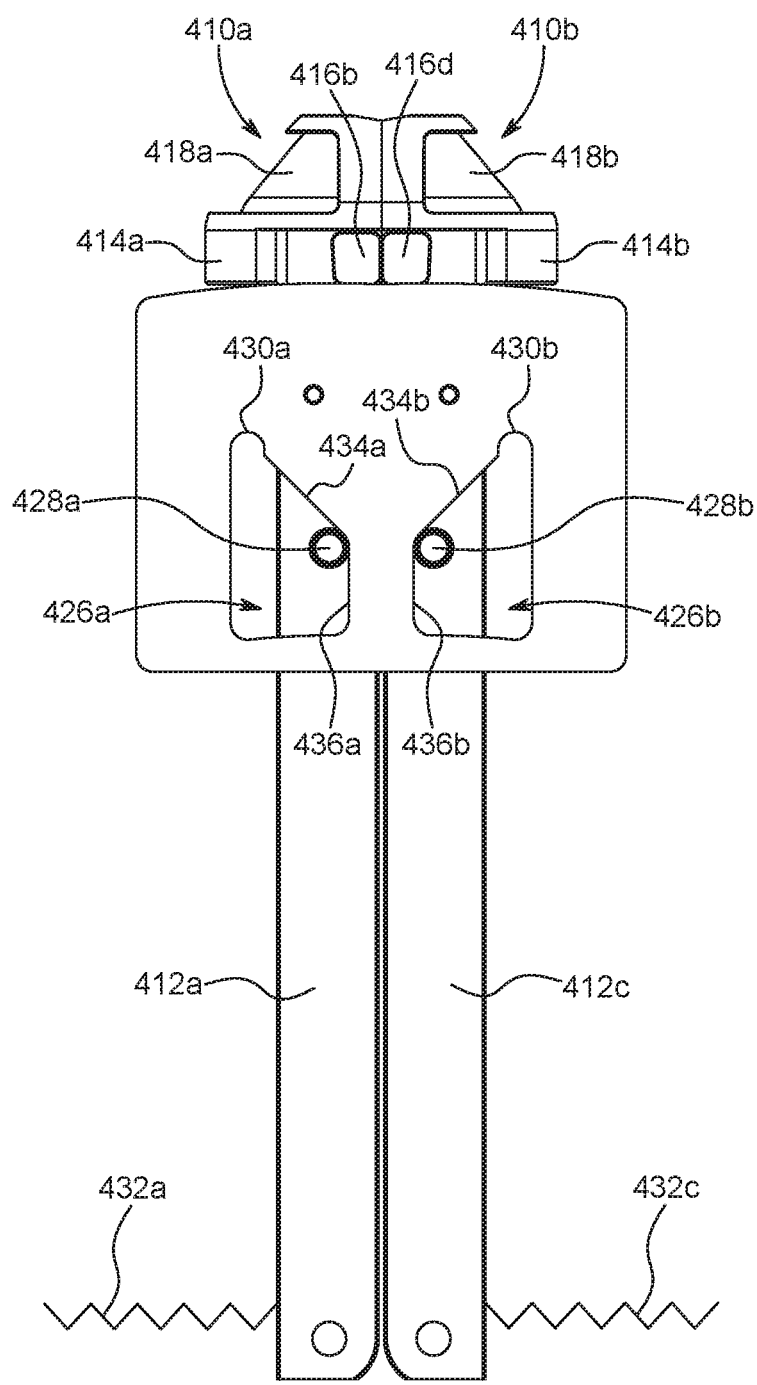
FIG. 16A is a side view of the retaining arms of FIG. 10 in the retaining position.
Figure 16B:
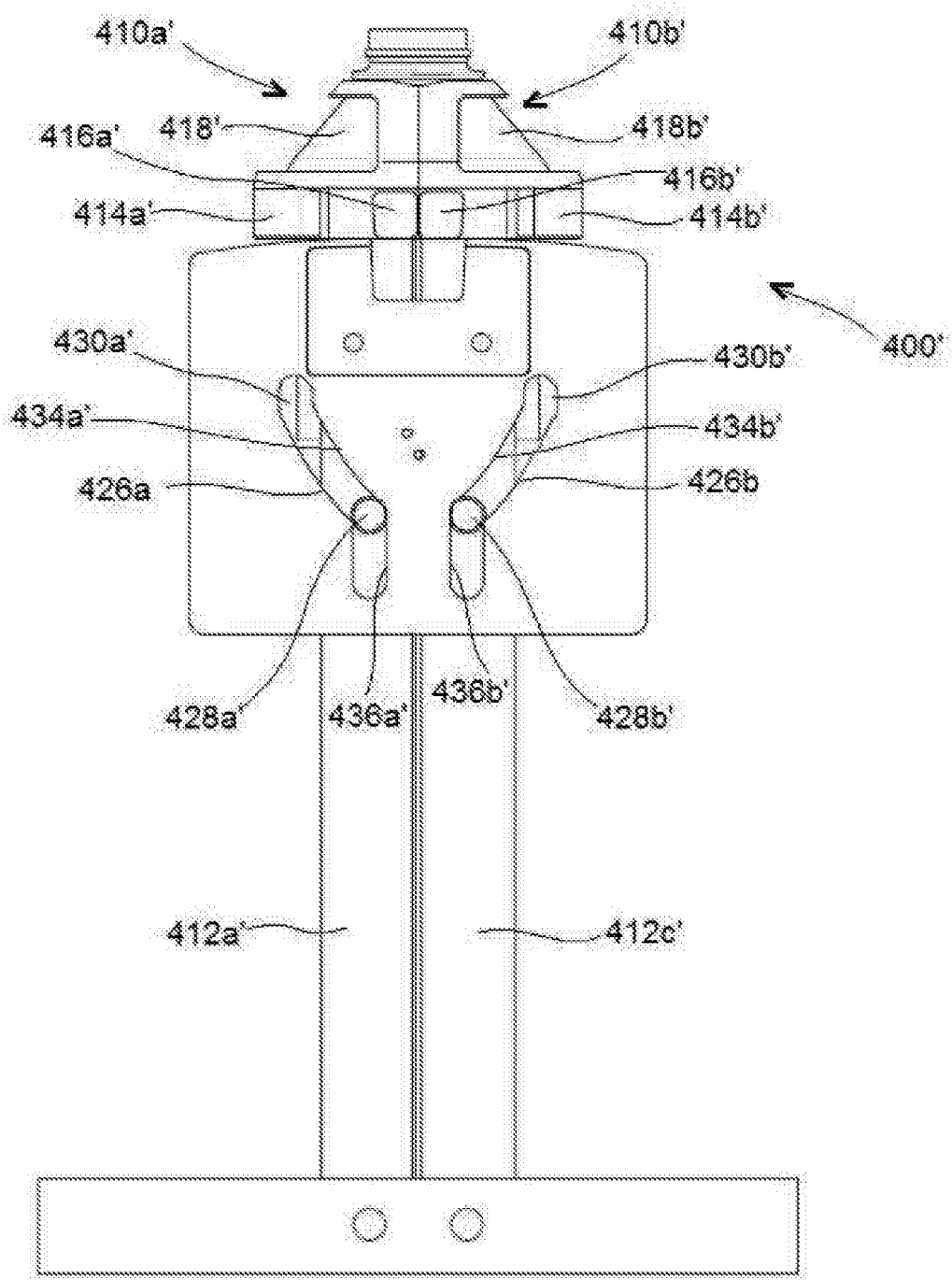
FIG. 16B illustrates a side view of an alternative cammed embodiment of the syringe retaining interface.

As shown in FIGS. 12 and 16A, after the syringe 132 has been inserted into the pressure jacket 308, the locking mechanism 420 may be moved in a distal or upward direction relative to the injector housing 102. As the locking mechanism 420 is moved distally, the compression springs 432a, 432b are configured to push the retaining arms 410a, 410*b* towards one another such that the pins 428*a*, 428*b* are directed along intermediate sloped portions 434*a*, 434*b* of the cam tracks 426*a*, 426*b*. The intermediate sloped portions 434*a*, 434*b* assist in gradually moving the retaining arms 410*a*, 410*b* towards one another to move into the second, closed position. As the retaining arms 410*a*, 410*b* come closer together, the pins 428*a*, 428*b* will transition from the intermediate sloped portions 434*a*, 434*b* to substantially vertical portions 436*a*, 436*b* of the cam tracks 426*a*, 426*b*. As shown in FIG. 16A, during transition of the pins 428*a*, 428*b* from the intermediate sloped portions 434*a*, 434*b* to the substantially vertical portions 436*a*, 436*b*, the retaining arms 410*a*, 410*b* will be brought into engagement in the second, retaining position such that the retaining elements 414*a*, 414*b* are positioned to limit the distal movement of the syringe 132.

Figure 17:
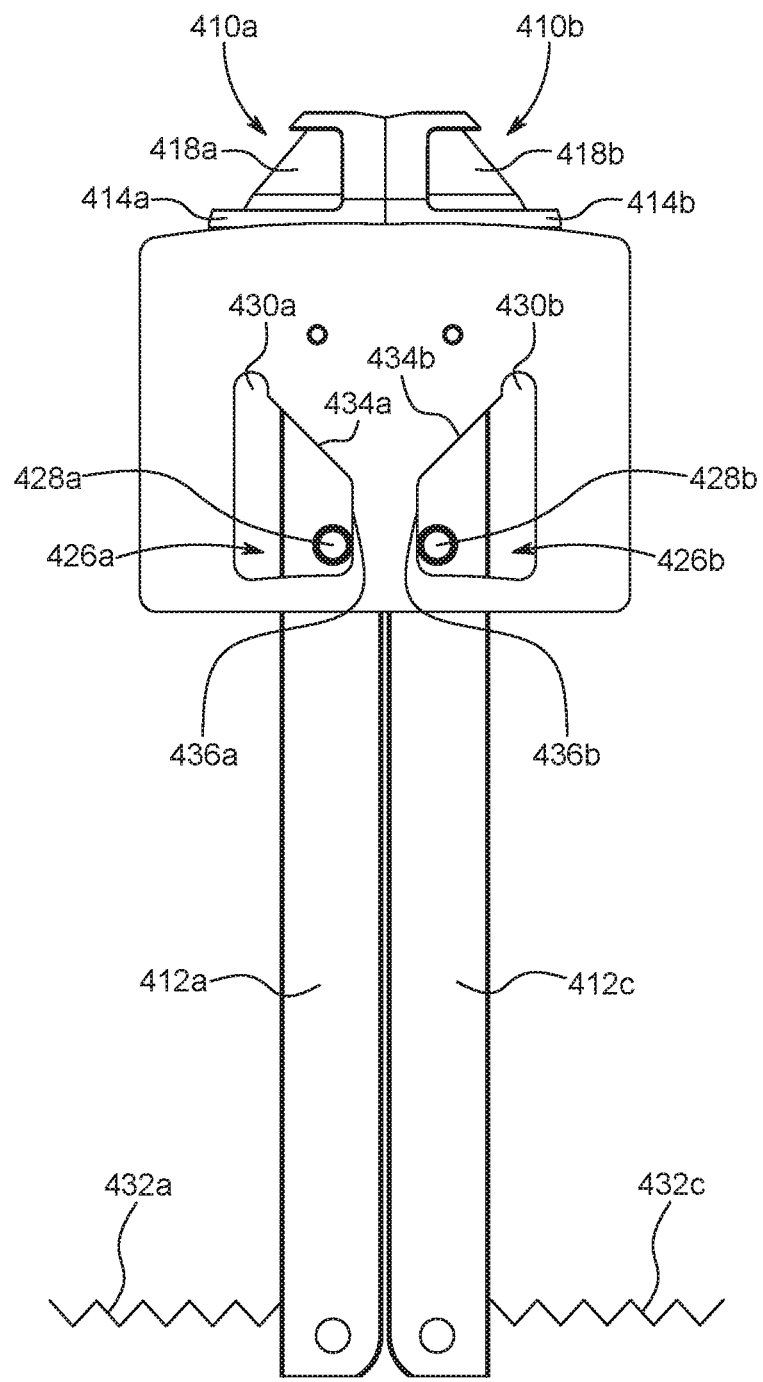
FIG. 17 is a side view of the retaining arms of FIG. 10 in the locking position.
Figure 18:
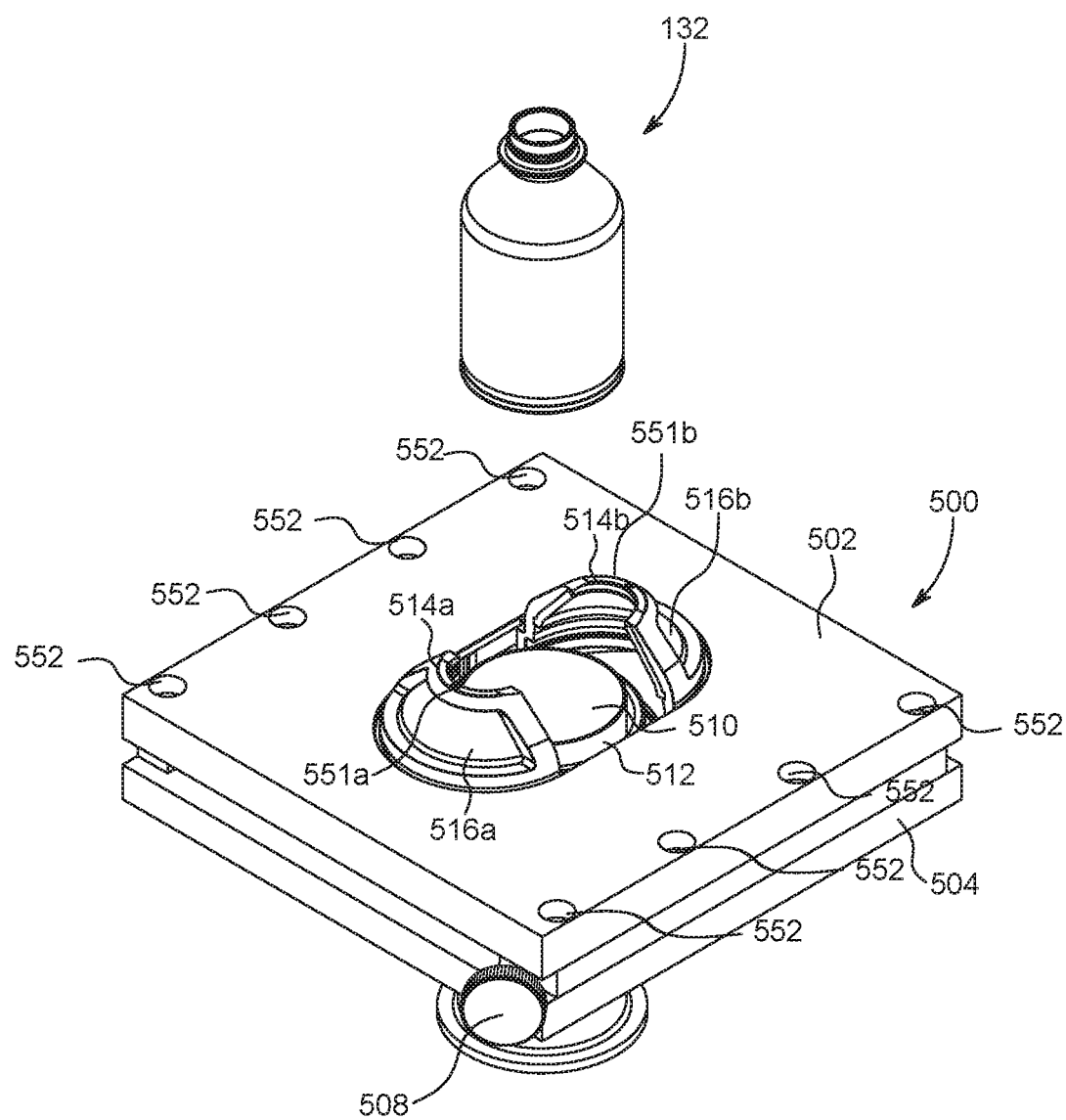
FIG. 18 is a perspective view of a syringe retaining interface according to another aspect of the present disclosure.

With reference to FIGS. 13 and 17, the locking mechanism 420 may then be moved farther in the distal or upward direction so the pins 428*a*, 428*b* move farther along the substantially vertical portions 436*a*, 436*b*. As the locking mechanism 420 continues to move in the distal direction, the locking protrusions 416*a*, 416*b*, 416*c*, 416*d* are moved into the locking grooves 424*a*, 424*b* in the locking mechanism 420. As described herein, once the locking protrusions 416*a*, 416*b*, 416*c*, 416*d* are positioned within the locking grooves 424*a*, 424*b*, the retaining arms 410*a*, 410*b* are prevented from moving radially in both an outward direction and an inward direction. In some examples or aspects, the outer edges of the locking protrusions 416*a*, 416*b*, 416*c*, 416*d* may be tapered to force the locking protrusions 416*a*, 416*b*, 416*c*, 416*d* and the retaining elements 414*a*, 414*b* into a firm, tight locking position. In another aspect, the locking protrusions 416*a*, 416*b*, 416*c*, 416*d* are designed to fit into the locking grooves 424*a*, 424*b* only if the retaining arms 410*a*, 410*b* are in the second, closed position. Therefore, if an obstruction is present between the retaining arms 410*a*, 410*b*, the locking protrusions 416*a*, 416*b*, 416*c*, 416*d* will interfere with portions of the two plate members 422*b*, 422*d* and will prevent the locking mechanism 420 from moving the retaining arms 410*a*, 410*b* into the second, closed position.

In some examples or aspects, shown in FIG. 13, at least one sensor 438 may be added to the locking mechanism 420 to determine the current state or position of the retaining arms 410*a*, 410*b* before the retaining arms 410*a*, 410*b* are locked. In some examples or aspects, the sensor 438 may be an optical sensor, make or break sensor, magnetic switch sensor, motor current or encoder sensor, a proximity sensor, or a motion sensor. The sensor 438 may be configured to detect when the retaining arms 410*a*, 410*b* have been moved into the second, closed position to indicate to the fluid injector system 100 whether the locking mechanism 420 is permitted to move in the distal direction to lock the retaining arms 410*a*, 410*b* and to initiate a fluid injection protocol, for example by starting a syringe filling process. In the event an obstruction is positioned between the retaining elements 414*a*, 414*b* and is preventing the retaining arms 410*a*, 410*b* from moving into the second, closed position, the sensor 438 will not be activated or will send a signal to the processor indicating that the retaining elements 414*a*, 414*b* are not closed and, therefore, the fluid injector system 100 will be prevented from moving the locking mechanism 420 in the distal direction until the obstruction is removed and the locking mechanism 420 can be moved into the locked position, locking the retaining arms 410*a*, 410*b* in the second, closed position.

Once the retaining arms 410*a*, 410*b* are locked in the second, retaining position, the retaining elements 414*a*, 414*b* constrain the syringe 132 within the pressure jacket 408 by opposing an upward or distal force applied to the syringe 132 during an injection procedure. Furthermore, the retaining elements 414*a*, 414*b* minimize syringe compliance by supporting the conical distal portion 140 of the syringe 132 and preventing the conical distal portion 140 of the syringe 132 abutting the retaining elements 414*a*, 414*b* from expanding/swelling due to the pressure exerted during the injection procedure. The extension members 412*a*, 412*b*, 412*c*, 412*d* may assist in transferring the distal axial force exerted on the syringe 132 downward to the base of the injector housing 102, while any radial expansion forces at the conical distal portion 140 of the syringe 132 are resisted by the locking mechanism 420. The extension members 412*a*, 412*b*, 412*c*, 412*d* may also assist in transmitting a tensile load from the extension members 412*a*, 412*b*, 412*c*, 412*d* to the base 402 through pins 401*a*, 401*b*, 401*c*, 410*d* provided at the proximal ends of the extension members 412*a*, 412*b*, 412*c*, 412*d*. In certain embodiments, the retaining elements 414*a*, 414*b* may include a slot for receiving at least a portion of a syringe flange 133 when in the second closed position to limit proximal movement of the syringe 132 during a piston/end wall or piston/plunger retraction process. Alternatively, abutment of the proximal surface of syringe flange 133 against the distal surface 451*a*, 451*b* combined retaining elements 414*a*, 414*b* limit proximal movement of the syringe during a piston/end wall or piston/plunger retraction process.

With reference to FIGS. 18 to 24, another example or aspect of a syringe retaining interface 500 according to the present disclosure is illustrated. The syringe retaining interface 500 may be provided on the top plate 302 of an injector housing 102 to limit the movement of the syringe 132 in the distal and proximal directions during an injection procedure of the fluid injector system 100. The syringe retaining interface 500 may include a top body member 502, a bottom body member 504, and a cam plate 506 (shown in FIG. 21) operatively positioned between the top body member 502 and the bottom body member 504. The top body member 502 and the bottom body member 504 may be solid plate members operatively connected to one another, for example by at least one screw 552. The cam plate 506 may be manually rotated within the top body member 502 and the bottom body member 504 via a knob 508 operatively connected to the cam plate 506. In another aspect, the cam plate 506 may be automatically rotated using a motor operated by a controller on the fluid injector system 100. The syringe retaining interface 500 may define an aperture 510 that may be configured to receive a syringe 132 within a pressure jacket 512 when the syringe 132 is inserted into the syringe retaining interface 500. The pressure jacket 512 may be operatively connected to the injector housing 102, as disclosed herein.

The syringe retaining interface 500 may also include at least two retaining elements 514*a*, 514*b*, which may be made of a plastic or metal, such as stainless steel, that may be configured to retain and hold the syringe 132 within the syringe retaining interface 500 during the injection procedure. The retaining elements 514*a*, 514*b* are operatively connected to the cam plate 506 and may be configured to move towards and away from one another upon rotation of the handle 508 or the cam mechanism. A proximal conical surface of retaining element 514*a*, 514*b* may be configured to abut the conical shape of the distal end 140 of the syringe 132. Each retaining element 514*a*, 514*b* may include a syringe cone support 516a, 516b that is positioned and held within the retaining elements 514a, 514b. At least a portion of the syringe cone supports 516a, 516b may be made of a transparent or translucent material, such as a polymeric material to support the distal portions of the syringe 132 and allow inspection of the distal portion of the syringe 132, as described herein. The retaining elements 514a, 514b may surround and stiffen the syringe cone supports 516a, 516b. The retaining elements 514a, 514b and the syringe cone supports 516a, 516b may be conical in shape to correspond to the conical shape of the distal end 140 of the syringe 132.

Figure 19:
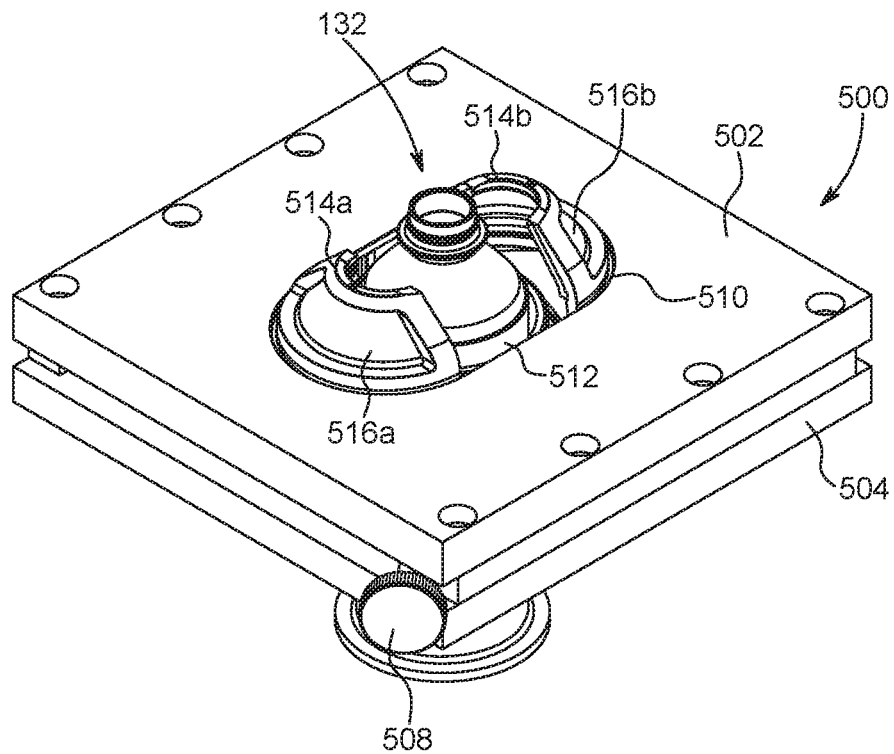
FIG. 19 is a perspective view of the syringe retaining interface of FIG. 18 with a syringe positioned therein.

As shown in FIG. 19, the syringe 132 may be inserted into the syringe retaining interface 500 past the retaining elements 514a, 514b. The retaining elements 514a, 514b have been separated from one another in a first open position, which permits the syringe 132 to be inserted into the pressure jacket 512 through the aperture 510. According to various embodiments, the handle 508 may be held or a processor may use a motor to maintain the syringe retaining interface 500 in the first open position to keep the retaining elements 514a, 514b separated from one another. As shown in FIG. 19, a gap established between the retaining elements 514a, 514b may be sufficiently wide enough to permit the syringe 132 to be inserted into the pressure jacket 512 through the aperture.

Figure 20:
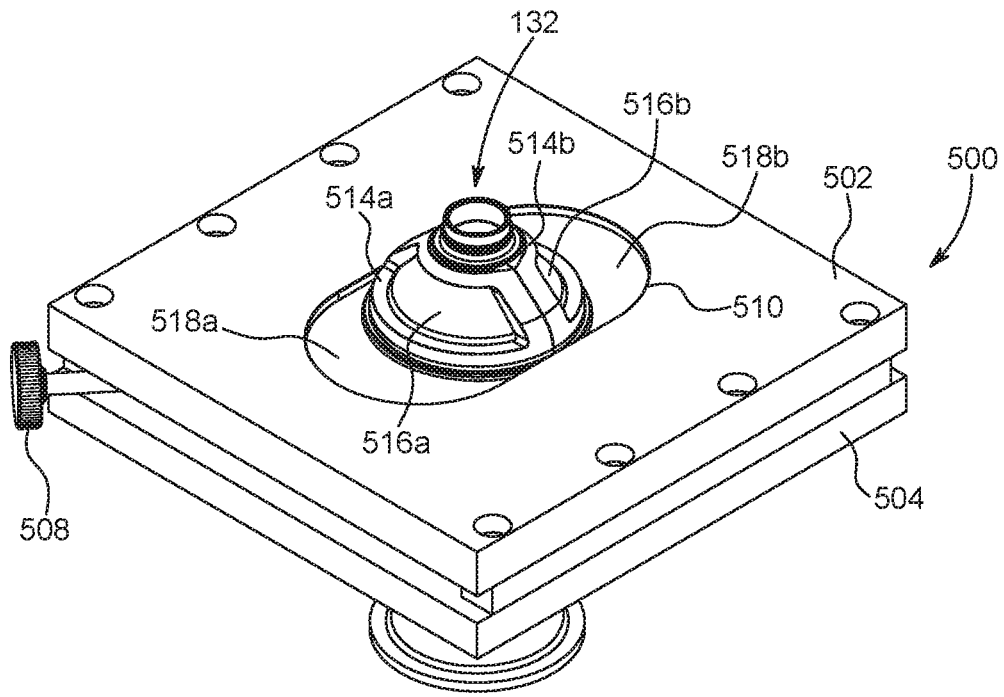
FIG. 20 is a perspective view of the syringe retaining interface of FIG. 18 in a retaining position.

With reference to FIG. 20, after the syringe 132 is inserted into the pressure jacket 132, the handle 508 may be rotated or a processor may move the syringe retaining interface 500 to a second closed position to force the retaining elements 514a, 514b towards one another to close the gap between one another. The handle 508 may be rotated manually or automatically using a controller on the fluid injection system 100 or a processor may utilize a motor to move close the aperture. The retaining elements 514a, 514b may be pushed into contact with one another to close the gap therebetween leaving an aperture of reduced diameter through which the distal tip of the syringe 132 may protrude, or the retaining elements 514a, 514b may be pushed together such that a negligible gap is left between the two retaining elements 514a, 514b. When the retaining elements 514a, 514b are pushed into this second, closed position, the retaining elements 514a, 514b cover the distal end portion of the syringe 132 to limit movement of the syringe 132 in a distal direction relative to the injector housing 102 or the syringe retaining interface 500 during an injection procedure of the fluid injector system 100. Further, a distal circumferential surface of retaining elements 514a, 514b may abut a proximal surface of syringe flange 133 to support the syringe 132 and limit proximal movement of the syringe during a filling procedure. Therefore, the retaining elements 514a, 514b provide axial and radial support to the syringe 132. Furthermore, the retaining elements 514a, 514b assist in carrying an axial load from the retaining elements 514a, 514b to the bottom body member 504. With further reference to FIG. 20, after the retaining elements 514a, 514b have been moved into the second, closed position, a guide surface 518a, 518b operatively connected to a respective retaining element 514a, 514b extends to the aperture 510. By extending the guide surfaces 518a, 518b to the aperture 510 and the portions of the retaining elements 514a, 514b, the guide surfaces 518a, 518b fill in any gaps that may be left by moving the retaining elements 514a, 514b towards one another, thereby preventing any fluids or debris from falling through the aperture 510 into the syringe retaining interface 500 and possibly the injector housing 102. The handle 508 may be moved between the first open position and second closed position to move the retaining elements 514a, 514b towards and away from one another. In some examples or aspects, the handle 508 or cam system may be locked when provided in the first open position or the second closed position so that the handle 508 is not inadvertently moved. In other embodiments, movement of the retaining elements 514a, 514b is controlled by the processor through a motor.

Figure 21:
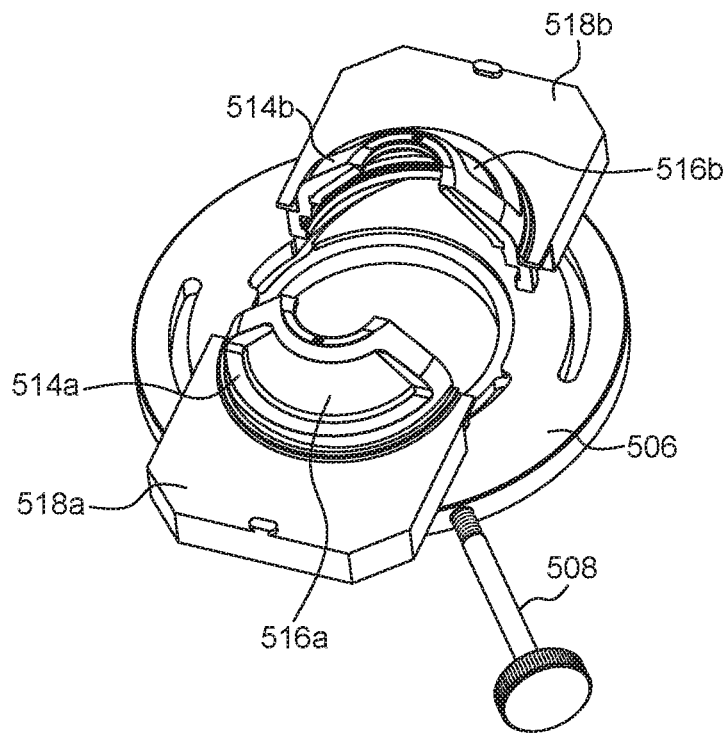
FIG. 21 is a perspective view of retaining elements of the syringe retaining interface of FIG. 18 shown in an open position.
Figure 22:
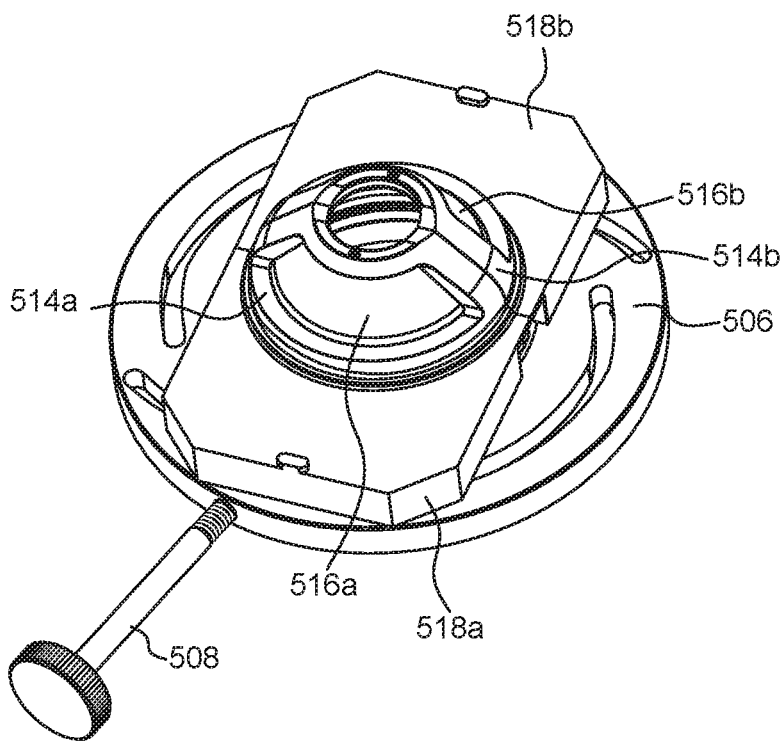
FIG. 22 is a perspective view of the retaining elements of FIG. 21 shown in a retaining position.

With reference to FIG. 21, the internal components of the syringe retaining interface 500 are shown. The cam plate 506 may be rotated, for example, using the handle 508, which in turn moves the retaining elements 514a, 514b towards and away from one another utilizing a cam mechanism as described herein. Handle 508 is shown in the first open position in FIG. 21, with retaining elements 514a, 514b separated from one another. Referring to FIG. 22, the handle 508 is in the second position and retaining elements 514a, 514b are moved towards one another into the second, closed position.

Figure 23:
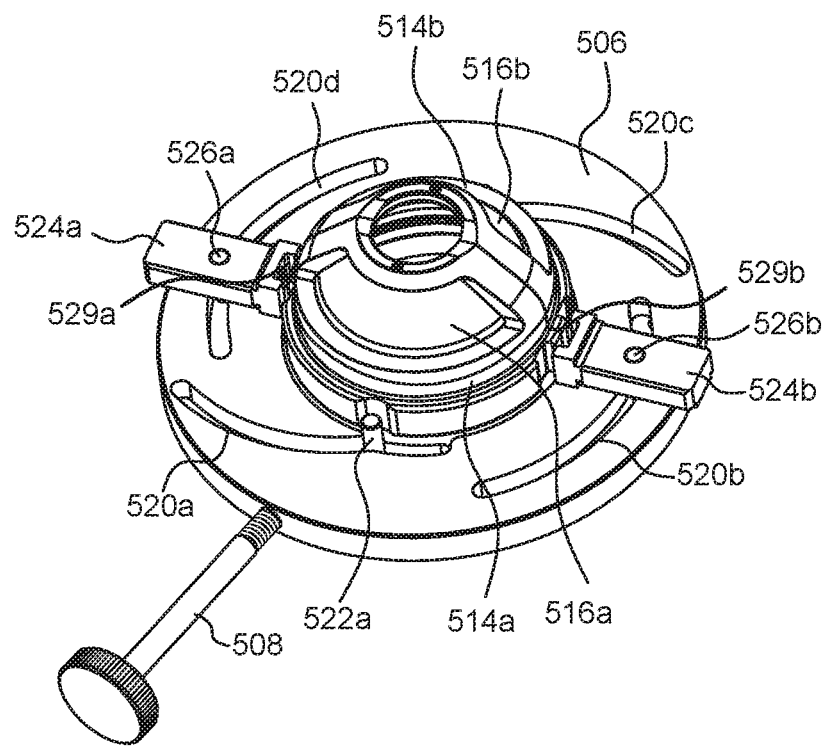
FIG. 23 is another perspective view of the retaining elements of FIG. 21 shown in the retaining position.
Figure 24:
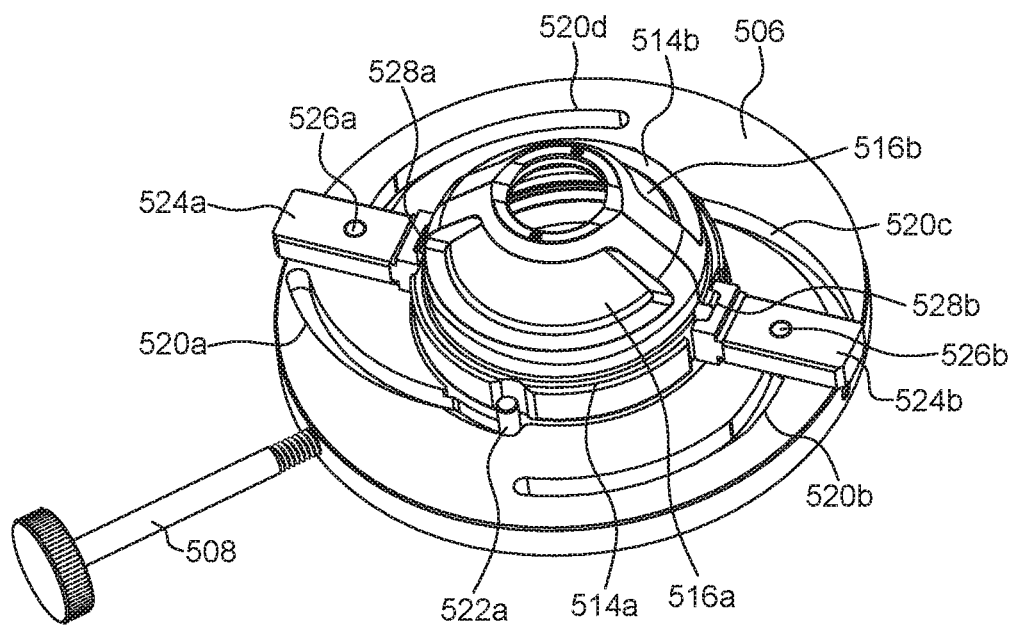
FIG. 24 is a perspective view of the retaining elements of FIG. 21 shown in a locking position.

With reference to FIGS. 23 and 24, the operation and locking mechanism of the syringe retaining interface 500 and, in particular, the cam plate 506 are further described. The guide members 518a, 518b of the retaining elements 514a, 514b have been removed from the figures for clarity. The cam plate 506 may define two or more grooves, such as the four separate grooves 520a, 520b, 520c, 520d illustrated in FIGS. 23 and 24 used to move the retaining elements 514a, 514b towards and away from one another and to lock the retaining elements 514a, 514b when in the second closed position. As shown in FIG. 23, a guide pin 522a may be operatively connected to each respective guide member 518a, 518b. FIG. 23 does not show the corresponding guide pin for the guide member 518b, but would be operatively connected to and move in a similar manner as the guide pin 522a connected to the guide member 518a. When the guide pins 522a, 522b are positioned in a radially outermost end of the respective grooves 520a, 520c, the retaining elements 514a, 514b are separated from one another in the first open position since the guide pins 522a, 522b pull the retaining elements 514a, 514b in an outward direction.

As the handle 508 or cam system is rotated to the second closed position, the guide pins 522a, 522b are moved from the outermost end of grooves 520a, 520c to an innermost end of grooves 520a, 520c. As the guide pins 522a, 522b are moved from the outermost end to an innermost end of the grooves 520a, 520c, guide pins 522a, 522b move the respective guide member 518a, 518b inwardly towards the opposing guide member.

With reference to FIGS. 23 and 24, further locking features of the syringe retaining interface 500 are illustrated. The syringe retaining interface 500 may also include at least two cam operated locking members 524a, 524b provided on cam plate 506. Similar to the retaining elements 514a, 514b, the locking members 524a, 524a may be configured to move towards and away from one another during rotation of the cam plate 506. Each locking member 524a, 524b may include a guide pin 526a, 526b that is received in a cam groove 520b, 520d of the cam plate 506. The guide pins 526a, 526b are configured to move within grooves 520b, 520d to slide locking members 524a, 524b towards and away from retaining keys 529a, 529b on retaining elements 514a, 514b. The locking members 524a, 524b are configured to move between a first, unlocked position and a second, locked position.

During the rotation of the handle 508 from the first open position to the second, closed position, the guide pins 526a, 526b initially move along the grooves 520b, 520d but do not move the locking members 524a, 524b towards the retaining elements 514a, 514b. After the handle 508 has been moved to the second, closed position and the retaining elements 514a, 514b are positioned in the retaining position, the handle 508 may be further rotated to cause the guide pins 526a, 526b to move farther along the grooves 520b, 520d. In some examples or aspects of the present disclosure, the handle 508 may be rotated an additional angle to move the locking members 524a, 524b into a locked position with locking keys 529a, 529b. Due to the inclination of the end of the grooves 520b, 520d, the guide pins 526a, 526b are moved inwardly towards the retaining elements 514a, 514b, thereby causing the locking members 524a, 524b to move towards the locking keys 529a, 529b of retaining elements 514a, 514b. The radially outwardmost end portions of the grooves 520a, 520c for the guide pins 522a of the retaining elements 514a, 514b may retain a constant radius such that, as the handle 508 is further rotated, the retaining elements 514a, 514b are no longer pushed towards the retaining elements 514a, 514b. Each end of the grooves 520b, 520d may also include a constant radius that prevents reaction loads (due to the locking preload) from "back-driving" the guide pins 526a, 526b against the grooves 520b, 520d. With reference to FIG. 24, as the locking members 524a, 524b are moved towards the retaining elements 514a, 514b, locking grooves 528a, 528b defined in the locking members 524a, 524b receive portions of the each of the retaining elements 514a, 514b. With the locking grooves 528a, 528b receiving locking keys 529a, 529b of retaining elements 514a, 514b, the retaining elements 514a, 514b are prevented from separating from one another. Therefore, in one example or aspect of the present disclosure, the only way to separate the retaining elements 514a, 514b is to rotate the handle 508 back to the first, open position. In one example or aspect of the present disclosure, inner surfaces of the locking grooves 528a, 528b may be tapered that creates a wedging action that permits an interference or preload to be applied to the locking members 524a, 524b. Further, by receiving locking keys 529a, 529b of retaining elements 514a, 514b directly within the locking grooves 528a, 528b, the locking forces of the locking members 524a, 524b are applied directly to the retaining elements 514a, 514b without having to pass through intermediate components. Therefore, the locking members 524a, 524b prevent the retaining elements 514a, 514b from separating due to radial loads.

While various examples of the present invention were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. An injector system for delivering a medical fluid, the injector system comprising:
    an injector configured to receive at least one syringe, the injector comprising at least one piston for releasably engaging and reciprocally driving a plunger or an end wall of the at least one syringe; and
    a syringe retaining interface comprising a bracket that houses one or more retaining elements configured to engage at least a portion of a distal end portion of the at least one syringe to limit movement of the at least one syringe in a distal direction relative to the injector as the medical fluid is delivered from a reservoir via distal movement of the at least one piston,
    wherein the one or more retaining elements comprises slidable arms configured to be movable in a lateral direction relative to the longitudinal axis of the at least one syringe.

2. The injector system of claim 1, wherein the one or more retaining elements are configured to engage a flange on the distal end portion of the at least one syringe.

3. The injector system of claim 2, wherein each retaining element comprises a first surface configured to engage a distal surface of the flange and a second surface to engage a proximal surface of the flange.

4. The injector system of claim 1, wherein the one or more retaining elements are configured to engage at least a portion of a conical portion of the distal end portion of the at least one syringe.

5. The injector system of claim 1, wherein the slidable arms are movable laterally relative to the distal end portion of the at least one syringe between a first position, in which the slidable arms are disengaged from the at least a portion of the distal end portion of the at least one syringe, and a second position, in which the slidable arms are engaged with the at least a portion of the distal end portion of the at least one syringe to limit movement of the at least one syringe in the distal direction relative to the injector.

6. The injector system of claim 1, wherein the slidable arms are movable laterally relative to the distal end portion of the at least one syringe between a first position, in which the slidable arms define an aperture that has a diameter larger than an outer diameter of the at least one syringe, and a second position, in which the diameter of the aperture is smaller than the outer diameter of the at least one syringe such that the slidable arms limit movement of the at least one syringe in the distal direction relative to the injector.

7. The injector system of claim 1, wherein the one or more retaining elements are activated manually by an operator or automatically using at least one processor programmed or configured to operate activation of the one or more retaining elements.

8. The injector system of claim 1, wherein the syringe retaining interface comprises a rotating arm operatively connected to the injector, the rotating arm being rotatable about a longitudinal axis of the injector, and
    wherein the rotating arm includes the one or more retaining elements to engage the at least a portion of the distal end portion of the at least one syringe,
    wherein the rotating arm is configured to rotate between a first position, in which the one or more retaining elements are disengaged from the at least a portion of the distal end portion of the at least one syringe, and a second position, in which the retaining elements are engaged with the at least a portion of the distal end portion of the at least one syringe to limit movement of the at least one syringe in the distal direction relative to the injector.

9. The injector system of claim 8, wherein each of the one or more retaining elements comprises at least one of a cap holding arm and a flange holding arm, and
    wherein, when the rotating arm is positioned to engage the at least a portion of the distal end portion of the at least one syringe, the cap holding arm engages a cap of the at least one syringe and the flange holding arm engages a flange on the at least a portion of the distal end portion of the at least one syringe.

10. The injector system of claim 1, wherein the at least one syringe is a rolling diaphragm syringe comprising the end wall, wherein the rolling diaphragm syringe is received within a pressure jacket provided on the injector.

11. An injector system for delivering a medical fluid, the injector system comprising:
- an injector configured to receive at least one syringe, the injector comprising at least one piston for releasably engaging and reciprocally driving a plunger or an end wall of the at least one syringe; and
- a syringe retaining interface comprising a bracket that houses one or more retaining elements having a retaining surface contoured to engage at least a portion of a distal end conical portion of the at least one syringe to limit the movement of the at least one syringe in the distal direction relative to the injector as the medical fluid is delivered from a reservoir via distal movement of the at least one piston wherein the one or more retaining elements comprises slidable arms configured to be movable in a lateral direction relative to the longitudinal axis of the at least one syringe.

12. The injector system of claim 11, wherein the syringe retaining interface further comprises at least one locking protrusion provided on a distal end of each slidable arm, and
- wherein a locking mechanism defines at least one locking groove configured to receive at least one locking protrusion to prevent each slidable arms from separating from one another.

13. The injector system of claim 12, wherein the syringe retaining interface comprises at least two retaining elements, wherein the at least two retaining elements are operatively connected to a cam plate held on the injector.

14. The injector system of claim 13, wherein the cam plate is rotatable between a first position and a second position,
- wherein, as the cam plate is rotated from the first position to the second position, the at least two retaining elements engage the at least a portion of the distal end conical portion of the at least one syringe, and
- wherein, as the cam plate is rotated from the second position to the first position, the at least two retaining elements are disengaged from the at least a portion of the distal end cone portion of the at least one syringe.

15. The injector system of claim 13, wherein the syringe retaining interface further comprises corresponding locking sliders for each retaining element to lock the retaining elements in place after the retaining elements have engaged the distal end conical portion of the at least one syringe.

16. The injector system of claim 13, wherein the at least two retaining elements engage the distal end conical portion of the at least one syringe beneath a flange on the distal end cone portion of the at least one syringe.

17. The injector system of claim 11, wherein the syringe retaining interface further comprises at least one corresponding locking element for each retaining element to lock the retaining elements in place after the retaining elements have engaged the distal end conical portion of the at least one syringe.

18. A method of retaining at least one syringe on an injector, the method comprising:
- providing the injector comprising the at least one syringe;
- providing a syringe interface with a bracket that houses one or more retaining elements on the injector;
- moving the one or more retaining elements into a disengaged position to permit the at least one syringe to be inserted into the injector;
- inserting the at least one syringe into the injector; and
- moving the one or more retaining elements into an engaged position to engage at least a portion of a distal end portion of the at least one syringe to limit movement of the at least one syringe in a distal direction relative to the injector as medical fluid is delivered from a reservoir of the at least one syringe via distal movement of a plunger reciprocally movable in the reservoir of the at least one syringe wherein the one or more retaining elements comprises slidable arms configured to be movable in a lateral direction relative to the longitudinal axis of the at least one syringe.

19. The method of claim 18, wherein the one or more retaining elements are slid in the lateral direction when moving between the disengaged position and the engage position.

* * * * *

UNITED STATES PATENT AND TRADEMARK OFFICE
CERTIFICATE OF CORRECTION

PATENT NO. : 12,083,321 B2
APPLICATION NO. : 17/272401
DATED : September 10, 2024
INVENTOR(S) : Spohn et al.

It is certified that error appears in the above-identified patent and that said Letters Patent is hereby corrected as shown below:

In the Specification

In Column 4, Line 45, delete "engage" and insert -- engaged --, therefor.
In Column 7, Line 57, delete "engage" and insert -- engaged --, therefor.
In Column 8, Line 34, delete "positon:" and insert -- position; --, therefor.
In Column 10, Line 33, delete "during and" and insert -- during an --, therefor.
In Column 12, Line 67, delete "the fluid" and insert -- in the fluid --, therefor.
In Column 14, Line 5, delete "positon" and insert -- position --, therefor.
In Column 14, Line 37, delete "diameter" and insert -- diameter of --, therefor.
In Column 15, Line 58, delete "a the" and insert -- a --, therefor.
In Column 16, Line 5, delete "the a" and insert -- the --, therefor.
In Column 16, Line 22, delete "and a variety" and insert -- that a variety --, therefor.
In Column 18, Line 47, delete "unlocked positon" and insert -- unlocked position --, therefor.
In Column 20, Line 55, delete "434a ′ . 434b′′′" and insert -- 434a′ , 434b′ --, therefor.
In Column 24, Line 52, delete "524a, 524a" and insert -- 524a, 524b --, therefor.

In the Claims

In Column 26, Line 42, in Claim 8, delete "injector, and" and insert -- injector, --, therefor.
In Column 26, Line 45, in Claim 8, delete "syringe," and insert -- syringe, and --, therefor.
In Column 27, Line 23, in Claim 12, delete "arms" and insert -- arm --, therefor.
In Column 28, Line 37, in Claim 19, delete "engage" and insert -- engaged --, therefor.

Signed and Sealed this
Fifteenth Day of July, 2025

Coke Morgan Stewart
*Acting Director of the United States Patent and Trademark Office*